(12) United States Patent
Trogler et al.

(10) Patent No.: US 9,220,685 B2
(45) Date of Patent: *Dec. 29, 2015

(54) HOLLOW SILICA NANOSPHERES AND METHODS OF MAKING SAME

(71) Applicant: The Regents of the University of California, Oakland, CA (US)

(72) Inventors: William C. Trogler, Del Mar, CA (US); Sadik C. Esener, Solana Beach, CA (US); Davorka Messmer, San Diego, CA (US); Johan Ulrik Lind, Copenhagen E. (DK); Kristina K. P. Mitchell, San Diego, CA (US); Jian Yang, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 252 days.

This patent is subject to a terminal disclaimer.

(21) Appl. No.: 13/866,940

(22) Filed: Apr. 19, 2013

(65) Prior Publication Data

US 2013/0230570 A1 Sep. 5, 2013

Related U.S. Application Data

(63) Continuation of application No. 12/673,224, filed as application No. PCT/US2008/072972 on Aug. 13, 2008, now Pat. No. 8,440,229.

(60) Provisional application No. 60/955,678, filed on Aug. 14, 2007, provisional application No. 61/034,468, filed on Mar. 6, 2008.

(51) Int. Cl.
| | | |
|---|---|---|
| *A61K 9/14* | (2006.01) | |
| *A61K 9/00* | (2006.01) | |
| *A61K 9/51* | (2006.01) | |
| *A61K 39/00* | (2006.01) | |
| *A61K 47/48* | (2006.01) | |
| *A61K 48/00* | (2006.01) | |

(Continued)

(52) U.S. Cl.
CPC ............ *A61K 9/14* (2013.01); *A61K 9/0019* (2013.01); *A61K 9/5115* (2013.01); *A61K 9/5192* (2013.01); *A61K 39/0011* (2013.01); *A61K 47/48861* (2013.01); *A61K 47/48869* (2013.01); *A61K 48/0041* (2013.01); *B82Y 5/00* (2013.01); *C01B 33/12* (2013.01); *C01B 33/18* (2013.01); *C12N 15/87* (2013.01); *A61K 9/1611* (2013.01); *A61K 9/2009* (2013.01); *A61K 2039/53* (2013.01); *A61K 2039/6093* (2013.01); *Y10S 977/773* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 5,512,094 A | 4/1996 | Linton | |
| 6,221,326 B1 | 4/2001 | Amiche | |
| 8,440,229 B2 * | 5/2013 | Trogler et al. | ................. 424/489 |

OTHER PUBLICATIONS

Y Lu, J McLellan, Y Xia. "Synthesis and Crystallization of Hybrid Spherical Colloids Composed of Polystyrene Cores and Silica Shells." Langmuir, vol. 20, 2004, pp. 3464-3470.*

(Continued)

*Primary Examiner* — Isaac Shomer
(74) *Attorney, Agent, or Firm* — Perkins Coie LLP

(57) ABSTRACT

The disclosure provide hollow nanospheres and methods of making and using the same. The methods and compositions of the disclosure are useful for drug delivery and gene transfer.

23 Claims, 7 Drawing Sheets

(51) Int. Cl.
*B82Y 5/00* (2011.01)
*C01B 33/12* (2006.01)
*C01B 33/18* (2006.01)
*C12N 15/87* (2006.01)
*A61K 9/16* (2006.01)
*A61K 9/20* (2006.01)

(56) References Cited

OTHER PUBLICATIONS

Baharlou, Simin, International Preliminary Report on Patentability & Written Opinion, Date of Issuance of Report: Feb. 16, 2010, International Application No. PCT/US2008/072972.

Bunker et al., "Low-Temperature Stability and High-Temperature Reactivity of Iron-Based Core-Shell Nanoparticles," J. Am. Chem. Soc., 2004, pp. 10852-10853, vol. 126, No. 35.

Lee Sung Reol, International Search Report and Written Opinion, PCT/US08/072972, Feb. 18, 2009, Korean Intellectual Property Office.

Lu et al. "Synthesis and crystallization of hybrid spherical colloids composed of polystyrene cores and silica shells," Langmuir, American Chemical Society, 2004, pp. 3464-3470, vol. 20, No. 8.

Mori et al., "Organic-Inoorganic Nanoassembly Based on Complexation of Cationic Silica Nanoparticles and Weak Anionic Polyelectrolytes in Aqueous and Alcohol Media," Langmuir, vol. 20, 2004, pp. 1934-1944.

Parida et al., "Adsorption of organic molecules on silica surface," Advances in Colloid and Interface Science, 2006, vol. 121, Issue: 1-3, pp. 77-110.

* cited by examiner

HOLLOW SILICA NANOSPHERES AND METHODS OF MAKING SAME

CROSS-REFERENCE TO RELATED APPLICATIONS

This application is a continuation of U.S. application Ser. No. 12/673,224, filed Feb. 12, 2010, which is a U.S. National Stage Application filed under 35 U.S.C. §371, and claims priority to International Application No. PCT/US08/72972, filed Aug. 13, 2008, which application claims priority under 35 U.S.C. §119 to U.S. Provisional Application Ser. No. 60/955,678, filed Aug. 14, 2007, and to U.S. Provisional Application Ser. No. 61/034,468, filed Mar. 6, 2008, the disclosures of which are incorporated herein by reference.

STATEMENT REGARDING FEDERAL SPONSORED RESEARCH

This invention was made with government support under CA119335 awarded by National Institutes of Health. The government has certain rights in the invention.

FIELD OF THE INVENTION

The disclosure relates to nanostructures and methods of making and using the same. More particularly, the disclosure provides hollow nanospheres useful for drug delivery, imaging, gene transfer and sensing.

BACKGROUND

Traditional drug delivery methods, such as introducing plasma concentrations of drugs by injection, or inhalation and ingestion of drugs, can require repeated and relatively greater dosing, with problematic patient compliance. Chemotherapy, which applies these methods for cancer treatments, can adversely affect healthy cells thereby causing serious side effects. Compared with these methods, a controlled local release system provides the desired constant drug concentrations at the target specific areas of the body, lowers systemic drug levels and reduces the potential for harmful side effects. Many materials have been developed for drug delivery systems including liposomes, biodegraded polymer spheres, metal oxides, and other inorganic particles. Another advanced technology in the medical field is imaging with X-ray or magnetic contrast reagents.

Since chemotherapeutic agents have a reduced efficacy in non-proliferating cells, immunotherapy represents a valuable treatment option because it is able to eliminate tumor cells independent of their proliferative state. Tumor associated antigens have been identified for many tumors and those can serve as target for the immune system. One of the approaches used to induce immune responses against cancer cells are DNA vaccines. Injection of plasmids encoding polypeptides can induce immune responses against the transgene product, offering a potential means for immunization without requiring production and purification of complex antigens. Dendritic cells (DCs) are required to initiate the immune response to the transgene antigen(s) encoded by such DNA vaccines and cytotoxic T lymphocytes (CTLs) play a major role in eliminating malignant cells by specifically recognizing antigenic peptides presented on MHC class I molecules by dendritic cells (DC). DNA vaccines although showing some success, are not very efficient and new approaches are needed to improve efficacy.

SUMMARY

The disclosure demonstrates that "attachment" of DNA to hollow silica-NPs will increase DNA uptake by taking advantage the endocytic capacity of DCs. The data provided herein demonstrate that DCs readily take up DNA that has been adsorbed to hollow Silica-NPs and express the encoded transgene. The disclosure provides a multi-functional nanoparticle vaccine/therapy with good prospects for treatment and prevention of cancers including melanoma. The compositions and methods are scalable, single agent-multi-functional therapeutics. The approach is modular and useful for delivery of other tumor antigens to treat other cancers.

The disclosure provides methods of synthesis of monodisperse hollow porous nanoparticles and their application in targeted drug and gene delivery. By examining monodisperse nanoparticles, the influence of nanoparticle size on cellular uptake and in vivo transport can be examined, as well as potential imaging applications. A key aspect is the development of synthetic methods that permit differential chemical functionalization of the inner and outer surfaces of the nanoshells. The goals are to attach targeting ligands (e.g. integrins, targeting peptides, or antibodies) to the outer shell surface. The inner surface of the nanoshell will be tailored to have hydrophilic, hydrophobic, and acid base properties that optimize binding of a specific payload (e.g. drug, imaging agent, immune stimulant, quantum dot sensor). These have potential applications in cancer vaccines and drug therapies. The nanospheres will also be explored in diagnostic schemes as labeled carriers of PCR primer DNA in the development of array based analyses for determining genetic mutations in cancer cells. For surface functionalization of silica and titania nanospheres, as well as for surface modification of biosensing chips, air and water stable reagents for self-assembling monolayers are being prepared.

The disclosure demonstrates the synthesis of hollow porous silica and titania nanospheres in the about 20-1000 um range (e.g., about 40 nm to about 500 nm range) and shows their use as gene transfer agents and drug delivery agents to live cells. The data demonstrate the porosity of the nanoshell walls by heavy element staining and high resolution transmission electron microscopy. The cellular distribution of the nanoparticles in vivo was characterized by fluorescent imaging. The cellular distribution of nanoparticle payloads can be characterized by using two color labeling of the particle and payload. Quantum dots or metal nanoparticles contained within silica nanoshells can be synthesized. Chemistry techniques can be used to differentially functionalize the hollow nanoparticle inner and outer surfaces with hydrophobic and hydrophilic functional groups. In one aspect, the particles can be loaded and then a defined time release of doxorubicin from porous hollow nanoparticles can be achieved. Tumor targeting peptides can be used and attached to the surface of the nanoparticles for targeting in a cancer models. Fluorescently labeled nanospheres can be prepared as carriers of PCR primer DNA into microbubble reactors. In addition phosphonate polyethylene glycol (PPEG) reagents can be used as a coating for silica and titania nanospheres for improved in vivo biocompatibility. The disclosure demonstrates how to generated template synthesis of monodisperse hollow porous silica and titania nanoshells of 45 nm, 100 nm, 200 nm, and 500 nm diameters and with 3-5 nm thick porous walls; demonstrated uptake of fluorescently labeled 100 nm silica shells by live human dendritic cells with no cellular toxicity; demonstration of quantitative plasmid DNA binding to 100 nm silica spheres with the use of a cationic surface coating; synthesized surface functionalized silica nanospheres and demonstrated coupling of surface amino groups to fluorescent dyes; and synthesized phosphonate polyethylene glycol (PEG) reagents that allow coating self-assembled monolayers on silica and titania surfaces for nonbioadhesive surfaces on biosensor chips. Processing occurs in aerated aqueous solvents at neutral pH for easy and environmentally friendly processing.

The disclosure provides a method to synthesize a hollow silica nanosphere comprising: (a) synthesizing a precursor of silica shell by hydrolyzing a silicon-containing compound; (b) depositing the precursor of silica shell on a template particle using polyamino acids under neutral condition to give core-shell spheres; (c) removing the polystyrene core and polyamino acids by calcination or organic solvent to provide a hollow silica sphere. In one aspect, the calcination comprises heating the core-shell sphere to 450° C. In another aspect, the template particles comprise commercial amine functionalized polystyrene beads. In yet another aspect, the precursor of silica shell is deposited on the surface of an amine or carboxylate functionalized polystyrene or latex bead. The size of the template particle can be from about 40 nm to 1 um. In one aspect the silicon-containing compound is selected from the group consisting of tetraalkoxysilanes, trialkoxysilanes, dialkoxysilanes and any combination thereof. In another aspect the silicon-containing compound is selected from the group consisting of tetrapropoxysilane, tetraethoxysilane, tetramethoxysilane and any combination thereof. The silicon-containing compound can be hydrolyzed in acid solution (e.g., hydrochloric acid, sulfuric acid, nitric acid or any combination thereof). The silicon-containing compound can be hydrolyzed in 0.01M hydrochloric acid aqueous solution. In one aspect, the final concentration of the silicon-containing compound in the acids solution is 0.1-10M. In another aspect the final concentration of the silicon-containing compound in the acids solution is 1M. In another aspect the polyamino acids include monopolymer of amino acids with primary amine groups on the backbone in solid or aqueous solution. In another aspect the polyamino acids are 0.1% v/w aqueous solution of poly-L-lysine, poly-L-arginine and polyornithine. In yet another aspect, the silica shell deposits on the surface of polystyrene beads comprising a polyamino acid. In yet a further aspect, the deposit of silica shell on the surface of polystyrene is conducted at room temperature. In another aspect, the deposit of silica shell on the surface of polystyrene is conducted under a condition of pH range from 5.5 to 9.5. In yet another aspect, the deposit of silica shell on the surface of polystyrene is conducted under a condition of pH 7.4. In another aspect, the deposit of silica shell on the surface of polystyrene is conducted in phosphate buffer. In a further aspect, the polystyrene core is removed by heating the core-shell sphere in air at 400-900° C. for 3-6 hours. In one aspect, the heating temperature is achieved by employing a temperature ramp rate of from about 0.1° C./min to about 10° C./min. The polystyrene core can be removed by washing the core-shell spheres in organic solvents selected from the group consisting of toluene, dichloromethane, chloroform, tetrahydrofuran, dimethylformamide, and any combination thereof. In one aspect, the polystyrene core is removed by washing the core-shell spheres in toluene.

The disclosure also provides a hollow sphere made according a methods described above. In one aspect, the hollow sphere comprises a surface amino group or adsorbed polyamines as carriers of an oligonucleotide or polynucleotide. In another aspect, the hollow spheres are loaded with a biological agent. The biological agent can be a polynucleotide, oligonucleotide, small molecule agent, a peptide or polypeptide and the like. In another aspect, the hollow spheres can be formulated with a pharmaceutically acceptable carrier. The hollow sphere can be functionalized to associate the hollow sphere with a target analyte or cell The disclosure also provides methods of nucleic acid delivery comprising linking an oligonucleotide or polynucleotide to the hollow sphere of the disclosure and contacting a cell or subject with the hollow sphere-linked nucleic acid composition The disclosure also provides a use of polymer template core shell or hollow silica nanoparticles with surface amine groups or adsorbed polyamines as carriers of DNA for gene transfection.

The disclosure provides an optimized anti-tumor DNA vaccine using multifunctional nanoparticles. The hollow silica-NPs are expected to have very low toxicity and improved degradation profiles compared to solid particles. The methods and compositions of the disclosure demonstrate that these hollow silica-NPs readily form complexes with plasmid DNA and can enhance the uptake and expression of plasmid encoded genes by human dendritic cells (DCs).

In addition, the disclosure provides a peptide (Hp-91) derived from the endogenous molecule HMGB-1, that acts as a potent stimulus for DC activation and induction of CTL responses in both mouse and human systems.

Additional aspects of the invention will be understood from the description below, the attached drawings and the appended claims.

DESCRIPTION OF DRAWINGS

In FIGS. 6-8 uncharged is defined as 100 nm silica spheres with the polystyrene core removed by solvent extraction and charged spheres are defined as the 100 nm silica spheres with the polystyrene core removed by solvent extraction, but containing surface amino group by treatment with $(MeO)_3Si(CH_2)_3NH_2$.

DETAILED DESCRIPTION

Figure 1:
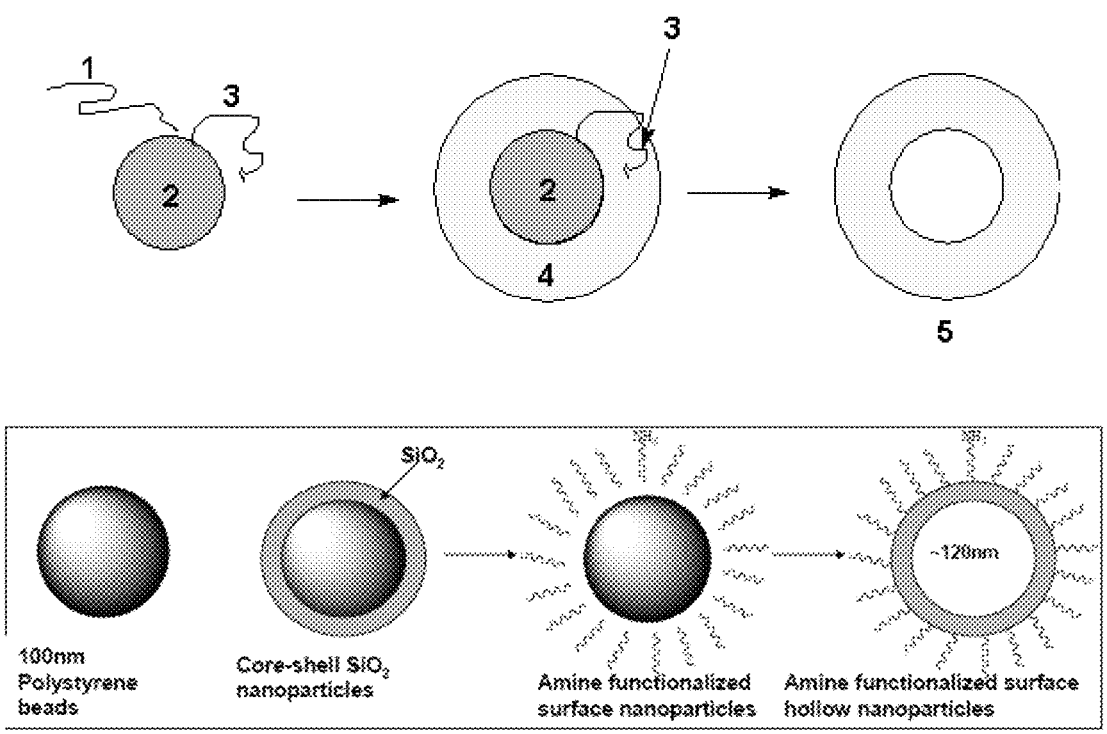
FIG. 1 is a schematic chemical reaction of one method of the disclosure. Schematic the chemical reaction of one method of the disclosure (1=silicic acid, 2=polystyrene or latex beads, 3=polyamino acid or polyamine coating to aid deposition of silica shell, 4=silica shell, 5=hollow silica sphere). For titania spheres the added polyamino acid or polyamine coating is not needed and Ti(O-t-Bu)4 is the source titania for the solution reaction. Not to scale.

As used herein and in the appended claims, the singular forms "a," "and," and "the" include plural referents unless the context clearly dictates otherwise. Thus, for example, reference to "a nanoparticle" includes a plurality of such nanoparticle and reference to "the cell" includes reference to one or more cells known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

The disclosure provides hollow nanospheres, compositions comprising such hollow nanospheres and methods of using such hollow nanospheres.

Hollow silica nanospheres are potentially applicable to drug delivery and imaging. Hollow silica nanospheres have uniform and stable wall structures with excellent long term stability. Their size can be controlled by using polymer templates for their formation with well-defined diameters accessible from emulsion polymerization. The porosity of the silica shell is convenient for loading and releasing of drugs or used to contain a heavy element (e.g. metal nanoparticle) or magnetic oxides for X-ray or magnetic contrast reagents. The surface of the hollow silica shell is easily functionalized by grafting biofunctional groups that may combine with targeting proteins, antibodies, cells, or tissues.

Since chemotherapeutic agents have a reduced efficacy in non-proliferating cells, immunotherapy represents a valuable treatment option because it is able to eliminate tumor cells independent of their proliferative state. Tumor associate antigens have been identified for many tumors and those can serve as target for the immune system. One of the approaches used to induce immune responses against cancer cells are DNA vaccines. Injection of plasmids encoding cancer-related antigens or polypeptides can induce immune responses against the transgene product, offering a potential method for immunization without requiring production and purification of complex antigens. Dendritic cells (DCs) are required to initiate the immune response to the transgene antigen(s) encoded by such DNA vaccines and cytotoxic T lymphocytes (CTLs) play a major role in eliminating malignant cells by specifically recognizing antigenic peptides presented on MHC class I molecules by dendritic cells (DC). DNA vaccines although showing some success, are not very efficient and new approaches are needed to improve efficacy. Hollow silica nanoparticles can serve as a platform to deliver DNA vaccines.

Many methods have been employed to fabricate hollow silica spheres, such as colloidal templating and layer-by-layer (LbL) self-assembly techniques. Colloidal particles were used to make core-shell nanospheres of gold, silver, CdS, ZnS and polymer beads; however, the inorganic templates are difficult to remove from the core-shell spheres. For those hollow spheres templated with polymers, their size and uniformity depend on the species and density of the surface functional groups, which makes size control difficult. The basis of the LbL technique is the electrostatic attraction between the charged species deposited. But this method involves numerous synthetic steps which make large scale production impractical. The challenge of hollow silica nanoparticle technology is to find a convenient and inexpensive method to fabricate hollow silica nanospheres with uniform, stable shell walls, and at the same time this shell should have acceptable porosity and a narrow size distribution.

There is no scalable inexpensive method for making uniform size distributions of hollow nanoparticles. Current nanoparticles used for drug delivery and sensing are solid. Hollow nanoparticles offer the possibility of filling with a payload of drug, imaging agent, or other material. The outer and inner surfaces could also be differentially functionalized.

During the past decade, there has been intense interest about the fabrication of hollow $SiO_2$ nanoparticles because of their applications such as drug delivery, ultrasound imaging, catalyst, filters, photonic band gap materials. In reported fabrication protocols, colloidal templating and layer-by-layer (LbL) self-assembly technique are most usually used. Colloidal templates used include gold, silver, CdS, ZnS and polymer beads. Polystyrene (PS) beads are attractive nanoscale templates since they are inexpensive and their size is easily varied. Furthermore their surface can be functionalized by chemical and physical techniques. Finally they are well-suited to make hollow particles since the polystyrene template can easily be removed by calcination or dissolution. Calcination can remove the latex cores and give the hollow $SiO_2$ nanoparticles. For example, the size and the uniformity of the nanoparticles depend in-part upon the density of the surface functional groups which makes the size control difficult. Caruso et al reported the fabrication of hollow $SiO_2$ nanoparticles through the polymer templated electrostatic LbL self-assembly of $SiO_2$ colloid-polymer multilayers, followed by removal of the templated cores. In this study Caruso applied poly(diallyldimethylammonium chloride) (PDAD-MAC), a linear cationic polyelectrolyte to form the composite multilayer with 25 nm $SiO_2$ colloid. The size of these particles was generally 500 nm and the majority of shells were broken or collapsed when one $SiO_2$-PDADMAC layer was applied.

Poly-L-lysine (PL) is one of the simplest polyamino acids with a pH-dependent structure and has been applied in many biomimetic syntheses of ordered silica structure.

In addition to the methods of nucleic acid delivery described herein, the disclosure provides a method of synthesis of hollow silica nanospheres with controllable size and porous, stable and uniform walls, which are useful for drug delivery and imaging materials.

For example, the DNA-nanosphere complexes of the disclosure take advantage of the physiological function of a type of white blood cell, called dendritic cell (DC). DCs are important for initiation of immune responses. DCs do not take up non-complexed DNA, and the adsorbtion of DNA to different size nanospheres allows for effective uptake of DNA and gene expression. The methods and compositions of the disclosure provide for DNA expression in DCs using nanospheres resulting in minimal cell death and 3-fold more cells that express the transgene using 6-fold less DNA than current state of the art methods.

In one embodiment, the disclosure provides a hollow silica sphere made from a silicon-containing compound with silicon atoms derived from, for example, tetraalkoxysilanes, silicic acid, sodium silicate and the like. Tetraalkoxysilanes used in disclosure include, for example, tetrapropoxysilane, tetraethoxysilane and tetramethoxysilane. The disclosure can include other tetraalkoxysilanes, trialkoxysilanes or dialkoxysilanes. In one embodiment, the silicon-containing compound is hydrolyzed under acidic condition before it reacts to form a silica shell.

The disclosure further provides a method for synthesis of hollow silica spheres. Commercial polystyrene or latex beads and their amine or carboxylate functionalized derivatives can be used in the disclosure as templates. The polymer core template used in the disclosure can have a narrow size distribution and can be chosen from about 10 nm to about 1 μm (typically about 20-40, 40-60 or 80-100 nm, but may be larger). A polyamino acid (e.g., poly-L-lysine), or any other polyamine, can be used in the disclosure with the core template mixture. A silicon-containing compound is added to react under conditions that cause the deposition of a silica gel shell on the polystyrene beads to form a uniform silica layer on the template. The polyamino acids can be washed away after the reaction. The polystyrene core is then removed by calcinations or solvent extraction. Both methods of core removal provide a hollow silica sphere with a uniform, porous, stable silica shell.

The polystyrene beads and the polystyrene or latex beads with amine or carboxylate functionalized surfaces, which are used in disclosure, can be purchased from Polysciences Inc and Invitrogen Co. The size of templates can be 10 nm, 20 nm, 30 nm, 45 nm, 80 nm, 100 nm, 200 nm, 500 nm, 750 nm or 1000 nm and both smaller and larger sized templates can be used (e.g., from about 10 nm to 2000 nm). These beads are monodisperse microspheres and are packaged as 2.0-4.0% solids (w/v) aqueous suspensions. These polystyrene microspheres can also contain surface primary amine groups or surface carboxylate groups. The polymer beads may also contain a fluorescent dye or other chemical or particle. These sizes typically vary by about 10% from batch to batch of manufacturer. After coating using the methods of the disclosure the size increases by 10-15 nm, but solvent washing shrinks them slightly and those that are calcined shrink more. The larger ones tend to shrink more. This occurs due to partial dehydration, as the shell initially forms as a silica gel coating and on removal of water dehydration to silica of varying degrees of hydration occurs. After calcining they comprise rigid hollow balls of porous glass like silica that undergo no further or limited size change.

The disclosure provides for the use of polyamine or polyamino acid templates, which gives a high yield of well formed spheres. The polyamines used in disclosure are homopolymers of amino acids or aliphatic amines with primary amine groups on the polymer backbone. Such polyamino acids are poly-L-lysine, poly-L-arginine, and polyornithine, including solids or their aqueous solution, typically about a 0.1% poly-L-lysine aqueous solution. On type of homopolymer of aliphatic amine is polyethyleneimine. The polystyrene beads or latex beads themselves can template the deposition of a silica shell, but without the presence of polyamine these core-shell spheres have an irregular silica shell which collapses during the procedure for removing the cores. The concentration of polyamino acids used in the disclosure is kept at low levels to avoid the formation of solid silica spheres templated by polyamino acids alone, which occurs at higher polyamino acid concentrations.

As in the sketch of FIG. 1, the polystyrene or latex beads are mixed with polyamino acids or polyamine before the hydrolyzed tetraalkoxysilane solution is added. The dispersion of beads and 0.1% w/v polyamino acid aqueous solution are added to a phosphate buffer. The ratio of 0.1% w/v polyamino acids and the 2.75% w/v polystyrene beads is from 1:1 to 10:1 v/v and most preferably 4:1. The final concentration of the polystyrene beads in the buffer solution is from 1:1000 to 1:10000 w/v but typically about 1:666 w/v.

One method of the disclosure is depicted in FIG. 1. As shown in FIG. 1, tetraalkoxysilane is hydrolyzed under acidic conditions to form silicic acid (1). Then (1) is added to a mixture of polystyrene or latex beads (2) and polyamino acid or polyamine (3). By selecting appropriate reaction conditions such as temperature, pH, and reaction time the polycondensation of silicic acid occurs and a silica gel shell (4) is deposited on the polystyrene beads. The core-shell spheres are collected, washed and calcined at high temperature to remove the polymer core to give hollow silica (partially dehydrated silica gel) spheres (5).

One method of making a nanostructure of the disclosure is depicted in FIG. 1. Template particle 2 is used in the methods of the disclosure. The template particles can be, for example, a latex or polystyrene bead. The template particle 2 comprises a silicic acid moiety 1. The template particle 2 is then treated to comprise a polyamino acid or polyamine group 3. The polyamino acid or polyamine group facilitate silica deposition. A silica shell 4 is then deposited on the template 2. In one aspect, the template nanostructure is degraded to provide a hollow nanostructure of the invention. In other embodiments, the template nanostructure remains intact. For titania spheres the added polyamino acid or polyamine coating is not needed and Ti(O-t-Bu)$_4$ is the source titania for the solution reaction.

The nanostructures may be used with or without decomposing the template material. Batch fabrication is straightforward. The characteristics of the resulting hollow sphere make the nanostructures useful for application in molecular medicine and in ultrasensitive Raman, biomolecular, and cellular imaging.

Various polymers may be used as the template nanostructure in the generation of a nanostructure of the disclosure. For example, o-polyacrylamide and poly(vinyl chloride), poly(vinyl chloride) carboxylated, polystyrene, polypropylene and poly(vinyl chloride-co-vinyl acetate co-vinyl) alcohols, may be used.

The ready availability of monosized polystyrene spheres between 45 and 500 nm provide a mass produced template for the high yield synthesis of mono-dispersed hollow silica-NPs with porous shell walls. The polymer spheres readily adsorb a monolayer of poly-L-lysine and other amino polymers in aqueous solution, which then serve as a basic catalyst coating for the gelation of silicic acid (Scheme I).

Scheme I

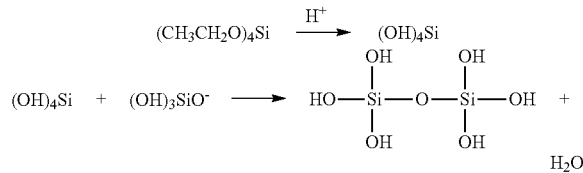

Figure 2:
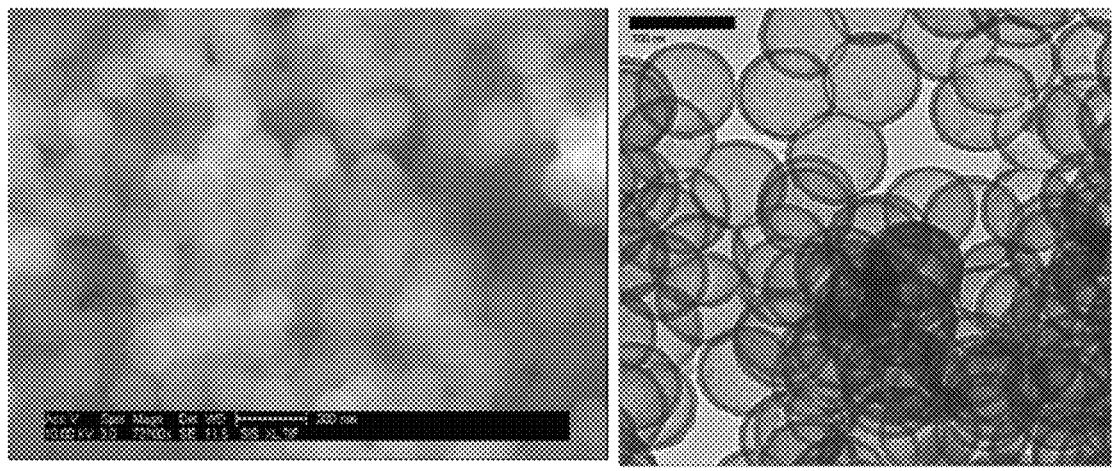
FIG. 2 is a photomicrograph of the core-shell polystyrene/silica spheres given by the method of the disclosure. (Left) Scanning electron microscope photomicrograph of core-shell silica nanoparticles template on 200 nm beads; (the scale bar is 200 nm). (Right) Transmission electron microscopy photo of hollow silica nanoparticles templated on 100 nm beads and calcined/burned to remove the polystyrene template; (the scale bar is 100 nm).

The positively charged poly-L-lysine chains in neutral buffer solution facilitate the polycondensation reaction of silicic acid. This rapidly yields a silica shell, which is similar to the neutral conditions used for polyamino acid templating of biosilica in organisms, such as diatoms. The silica gel forms around the poly-L-lysine in a thin (5-10 nm) layer on the outer surface of the polystyrene spheres. These particles can be isolated and partially dehydrated by extraction with anhydrous solvents, such as ethanol, to yield stable core shell particles. The polymer core can be loaded with fluorescent labels to track the location of the nanoparticles. Dynamic light scattering measurements confirm that the particles can be resuspended by mild ultrasonic agitation to produce aqueous colloidal dispersions with similar polydispersities as the original polymer beads. The core shell particles can be heated in air to 450° C., whereupon the polymer core and poly-L-lysine framework undergo complete oxidation to leave a hollow porous continguous silica gel nanoshell, which is slightly smaller than the polymer template. Dehydration of the silica shell on drying causes a slight shrinkage of the gel layer. The method of synthesis, SEM, and TEM images for two different sizes of hollow nanoparticles that have been prepared are shown in FIG. 2. Notice the high degree of reproducibility of the nanoshells in the bulk sample.

FIG. 2 shows a photomicrograph of the core-shell polystyrene/silica spheres synthesized by the method related to the disclosure. The core-shell spheres in the photomicrograph are templated by 100 nm amine functionalized polystyrene beads. After coating with the silica shell and drying in vacuum, the diameter of the core-shell spheres is 126±5 nm.

Fourier Transform Infrared Spectroscopy (FTIR) spectroscopy was also used to monitor removal of the polystyrene core. The C—H (Ar) and —CH$_2$— of the polystyrene stretching vibrations occur at 3030-2800 cm$^{-1}$. The absorption bands between 1480 and 1400 cm$^{-1}$ are from C—H bending vibrations. These features disappear completely after calcination. When using the dissolution method to remove the APS core, the FTIR spectrum shows that about 25% of the polystyrene remained. The amount of poly-L-lysine present in all cases was very low and the N—H stretches could not be observed before or after removal by calcination or organic solvents.

In the disclosure sodium phosphates can be used to make buffers with different pH. The concentration of the phosphates in buffer can be about 0.1M. The deposit of silica shell on polystyrene beads could be given at the pH range of from 5.5 to 9.5, but typically about pH 7.4. Other buffers can be used to modify the pH during silica shell formation.

After the polystyrene or latex beads and polyamino acid or polyamine are mixed in the phosphate buffer, hydrolyzed tetraalkoxysilane is added to the mixture to deposit silica shell on the beads. The addition of hydrolyzed tetraalkoxysilane is completed in one portion. The reaction is conducted on an agitator (e.g., a vortex agitator with the vortex speed of 3000 rpm, which provides vigorous rapid mixing). The vortex mixing time can be from about 2 minutes to 30 minutes, but is typically about 5 minutes. The core-shell spheres are evident by a cloudiness in solution in very short time. Prolonging the vortex mixing time did not increase the diameter of the core-shell spheres, which indicates that the formation of the silica shell on the polystyrene template occurs within a few minutes.

The reaction is typically conducted at room temperature. The final concentration of hydrolyzed tetraalkoxysilane in the reaction system is from about 10$^{-3}$M to 5×10$^{-3}$M and typically about 2×10$^{-3}$M. A useful concentration of hydrolyzed tetraalkoxysilane provides a uniform and stable silica shell around the templates with narrow size distribution range, and in high yield based on the template. Higher concentrations of hydrolyzed tetraalkoxysilane do not give a thicker silica shell but yield solid silica spheres as byproducts.

The core-shell spheres can be isolated from solution by centrifugation. The white precipitate can be washed by being dispersed in deionized water and centrifuged. These procedures are followed by washing the spheres with ethanol. These washing procedures in the disclosure are to remove excess reactant and phosphate buffer and are optional. After collection of the pure core-shell spheres by centrifugation, the polystyrene core can be removed, although it may not be desirable depending upon further processing or intended use.

Two methods can be used to remove the polystyrene core are calcination and dissolution, preferably the method of calcination. To remove the core by dissolution, the core-shell precipitate is suspended in toluene and the mixture is stirred 1 hour at room temperature and then collected by centrifugation. The washing procedure is repeated three more times and then the hollow spheres are washed twice with ethanol. The first solvent used in this step may be extended to dichloromethane, chloroform, ethylene diamine, tetrahydrofuran, or dimethylformamide. The final product of the disclosure is obtained by drying at 60° C. under vacuum for 48 hours. To remove the polystyrene cores by calcinations, the core-shell spheres are dried at 60° C. under vacuum for 48 hours, and then heated in air at 400-900° C. for 3-6 hours, more preferably heating at 450° C. for 4 hours. Temperature ramp and decline rates are from 0.1° C./min to 10° C./min, most preferably 5° C./min.

Hollow NP allow for independent surface conjugation of the exterior and interior surfaces. The hollow silica-NPs have uniform and stable wall structures with excellent stability for long term storage. Their size can be controlled by using polymer templates for their formation with well-defined diameters accessible from emulsion polymerization. The porosity of the silica shell is also convenient for loading of small molecules, such as drugs or short peptides in the core. The surface of the hollow silica-NPs is easily functionalized by grafting functional groups (e.g. amino groups as in Scheme II) that may combine with targeting proteins, antibodies, cells, or tissues. Hollow silica-NPs can also be made to contain other smaller nanoparticles, including Q-dots to monitor their position via fluorescence. Polystyrene beads were coated with poly-L-Lysine to template 100 nm core-shell silica-NPs; the surface was functionalized with $(MeO)_3Si(CH_2)_3NH_2$ either before or after the polymer core was removed by calcination or organic solvents (FIG. 1). For the calcinated particles, the surface coating is introduced at the end. The hollow Silica-NPs were functionalized with 3-aminopropyl(trimethoxy)silane as in Scheme II to add the additional amine groups. These are referred to as amine-modified silica-NPs. For example, 1 mg of calcinated hollow silica spheres, prepared from the 100 nm templates, was suspended in 2 mL of 1% 3-aminopropyl(trimethoxy)silane acetone solution. The mixture was stirred slowly for 2 hours with a magnetic stirrer followed by collecting the particles by centrifugation. The collected particles were washed with ethanol and dried in vacuum for 24 hours at room temperature. On a 100 nm sphere about 2400 or more surface attached amino groups can be obtained. Both small molecules and peptides containing a free carboxylic acid moiety can be coupled by the coupling reaction to the surface amines with EDAC (1-Ethyl-3-(3-dimethylaminopropyl)carbodiimide, hydrochloride) to form an amide bond.

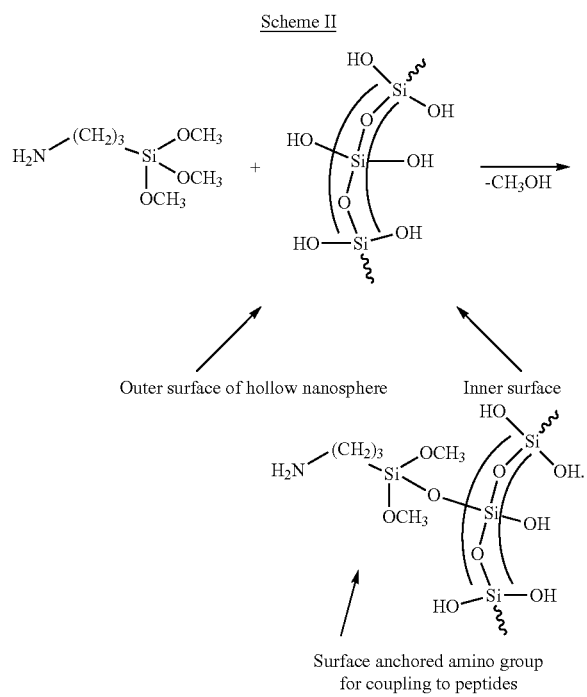

Figure 3:
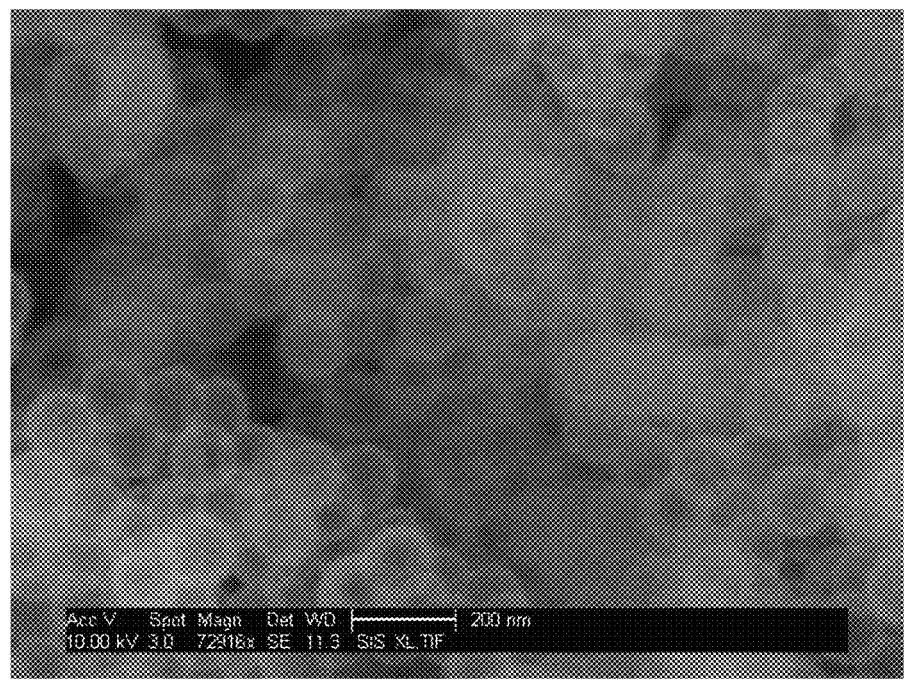
FIG. 3 is a photomicrograph of the hollow silica spheres given by the method of the disclosure. The silica shell is templated by 100 nm beads. (SEM instrument used)
Figure 4:
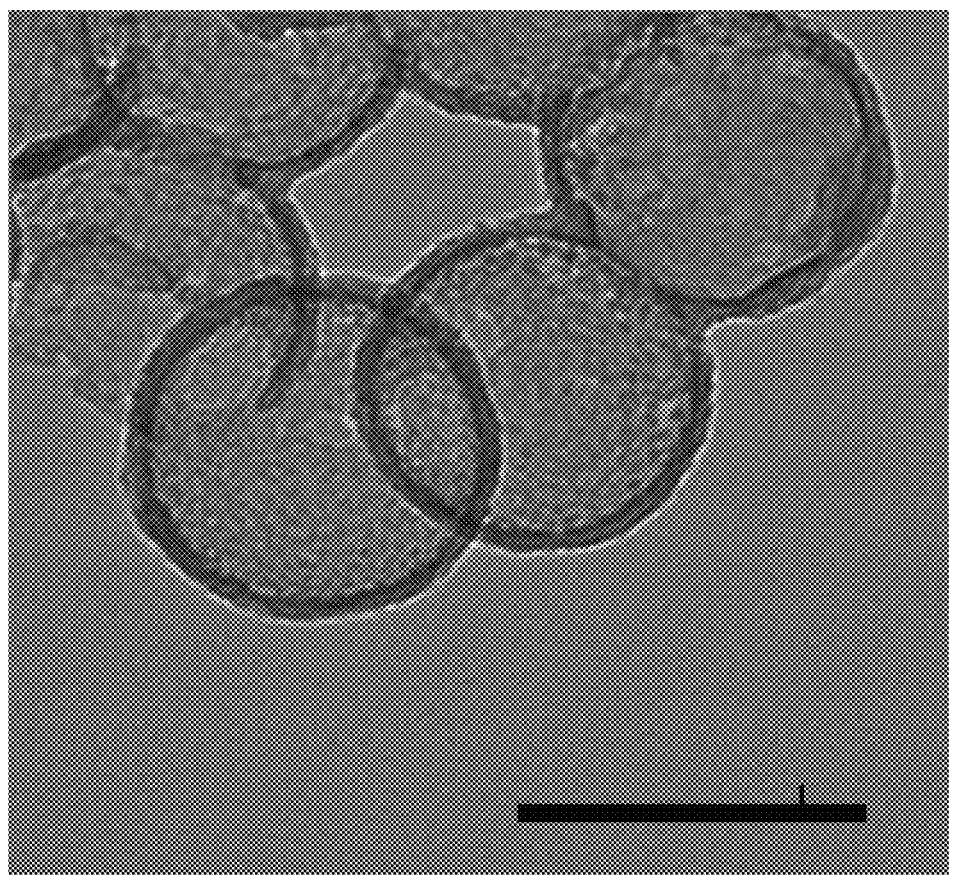
FIG. 4 is a photomicrograph of a hollow silica sphere given by the method of the present disclosure. The silica shell is templated by 100 nm beads. (TEM instrument used for image)
Figure 5:
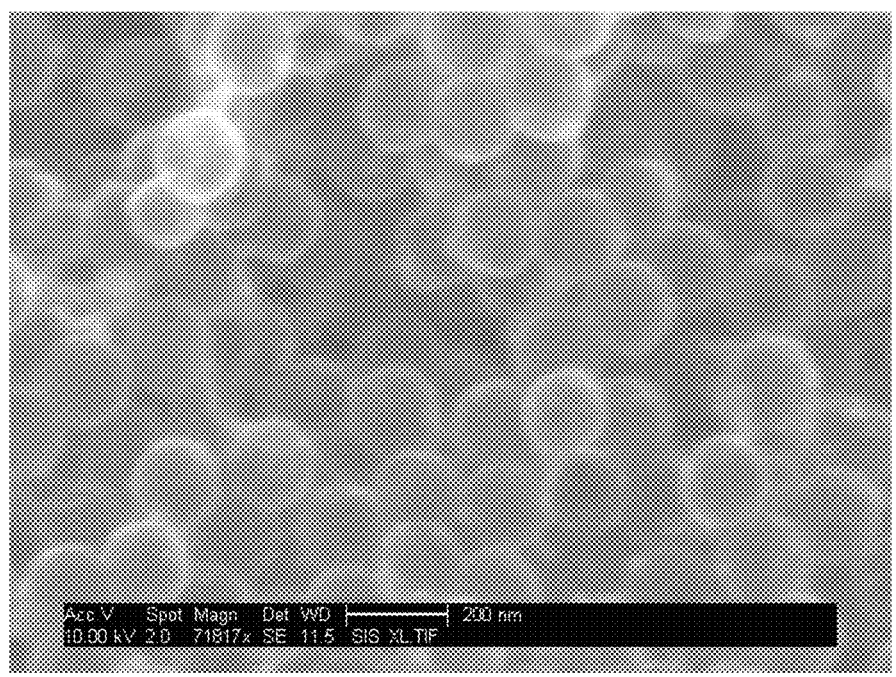
FIG. 5 is a photomicrograph of the hollow titania spheres prepared by the method of the disclosure. The titania shell shown is templated by 200 nm beads. (SEM instrument used)

FIG. 3 shows a photomicrograph of the hollow silica spheres given by the disclosure. The size of the hollow silica spheres is 205±7 nm. FIG. 4 is a photomicrograph of a hollow silica sphere. As FIG. 1 shows, the tetraalkoxysilane is hydrolyzed in aqueous acid solution. The acid used to hydrolyze the tetraalkoxysilanes is 0.01 M hydrochloric acid aqueous solution. In the disclosure the acids may be extended to sulfuric acid and nitric acid and by inference any other acid with a noninterfering anion. The tetraalkoxysilane could be tetrapropoxysilane, tetraethoxysilane or tetramethoxysilane, most preferably tetramethoxysilane. In the disclosure the precursor of silica shell may be extended to trialkoxysilanes or diaalkoxysilanes, and by inference any source of silicic acid could be used. The final concentration of tetraalkoxysilane in the acid is about 0.1-10M and but is typically about 1 M. The time of hydrolysis reaction is from about 5 minutes to 60 minutes, but typically about 15 minutes. The hydrolysis reaction is conducted at room temperature.

Table 1 shows the variation of the size of hollow silica spheres to the size of templates and the methods of removing the polystyrene cores. After removing templates the diameter of the silica shell shrinks, depending on conditions for core removal and template size. The hollow silica spheres made from large templates shrink more than those made from small templates. The hollow silica spheres obtained by calcination shrink more than those prepared by dissolution. The size distribution ranges of all of the hollow silica spheres made by the disclosure are less than 10%. Since the initially formed wall consists of silica gel, shrinkage of the wall is expected when the gel dries and partial dehydration occurs during calcinations or extractions with anhydrous solvents.

A final product of the disclosure is a white powder consisting of nanospheres that is easily suspended in deionized water, neutral phosphate buffer, methanol, ethanol, toluene or dichloromethane. Sonication for 15-30 minutes aids resuspension of the nanoparticles.

In the disclosure the hollow silica spheres obtained are functionalized with 3-aminopropyl(trimethoxy)silane. To do the functionalization the hollow silica spheres, after calcinations, are dipped in 1% 3-aminopropyl(trimethoxy)silane acetone solution. The ratio of hollow silica spheres and the 3-aminopropyl(trimethoxy)silane is from 1:10 to 1:100, preferably 1:20. The reaction is induced by a magnetic stirrer at room temperature and the reaction time is from about 30 minutes to 4 hours, typically about 2 hours. The amine functionalized hollow spheres are washed by deionized water and ethanol, followed by drying under vacuum at room temperature. The surface functionalization reaction can also be induced before removing the template with organic solvents. By this method the functionalized reaction occurs predominantly on the outside surface of the core-shell spheres. After removing the template the inside surface of the silica shell can be functionalized with different chemistry. Materials, which could react or interact with the surface of the hollow silica spheres are used for functionalization and, include trialkoxy- or triaryloxysilanes, dialkoxy- or diaryloxysilanes, alkoxy- or aryloxysilanes, derivatives thereof (i.e., oligametic or polymeric). For example, 3-mercaptopropyl(triethoxy)silane may react with the surface of hollow silica spheres and functionalize the surface with thiol groups. Amine groups or thiol groups on the surface of hollow silica spheres allow coupling with biomaterials, such as antibodies, proteins, enzymes, or DNA. After loading with drugs or heavy gas these kinds functionalized silica spheres may have diverse applications for targeted drug delivery or targeted contrast-enhanced imaging. In addition, the adsorptive properties of silica gel allow reversible adsorption of materials, as expected from the properties of silica gel like surfaces. The hollow nature of these nanoparticles also imparts them with a high surface area, as each particle contains an inner and outer surface.

The polystyrene beads or latex beads with amine functionalized surface could also be used as template to prepare hollow $TiO_2$ spheres using a similar procedure. The precursor of the $TiO_2$ shell is titanium t-butoxide. The synthesis of $TiO_2$ spheres is conducted in ethanol without the addition of polyamine. The ratio of template and titanium t-butoxide, the temperature and the time of reaction, and the method of removing the template are same as with the synthesis of silica spheres. Monodispersed hollow spheres with a uniform and porous $TiO_2$ wall are obtained with yield of 85-95%. Other metal alkoxides, which undergo sol-gel type reactivity are expected to react similarly and form hollow shells either with our without added polyamine template.

Some advantages of the disclosure are: using commercial polystyrene beads and their amine of carboxylate functionalized derivatives as templates to prepare silica nanoshells of uniform size with porous walls in high yield. These hollow nanoparticles could be prepared on a large scale and their size could be controlled from 40 nm to 1 um. The ability to surface functionalize the silica shell will allow diverse applications of the hollow silica nanospheres. Dissolution of the polymer core under mild conditions should allow differential functionalization of the hollow shell inner and outer surfaces.

The disclosure also provides a method to functionalize the surface of hollow silica spheres. For example, a 3-aminopropyl(trimethoxy)silane is used to react with the $SiO_2$ shell to provide an amine functionalized surface, which can then be crosslinked to proteins or used to adsorb DNA for diverse biological applications. This functionalization can be induced before or after removing of the template by organic solvents or after removing the template by calcination.

In yet another aspect, a metal particle or metal containing material can be incorporated into the hollow silica nanosphere. In this aspect, an aqueous colloidal suspension of a metal oxide nanoparticle precursor is added to a polyamino polystyrene composition, prior to contacting with a silicon containing compound.

The disclosure further provides a method for adsorbing DNA to hollow silica nanospheres. These complexes can be used to deliver oligonucleotide or polynucleotides (e.g., DNA or RNA or analogs thereof) into mammalian cells in a tissue culture dish for transgene expression as well as for vaccine purposes in vivo. For example, the DNA can encodes genes for cancer vaccines or viral or bacterial vaccines for prevention and therapy.

The disclosure provides nanostructures that are biocompatible and can be "loaded" with biological agents or other materials (e.g., drugs, metallic compositions, magnetic compositions and the like).

Although the specific examples provided herein demonstrate particular aspects of the hollow nanostructure of the disclosure, one of skill in the art will recognize that the size, shape, and layer thickness can all be individually controlled. Owing to its hollowness, the inner and outer surfaces can be modified with different materials for a wide variety of characteristics and functions.

The nanostructures of the disclosure are biocompatible, and thus can be biofunctionalized and applied in real-time biomolecular imaging as well as drug delivery. The term "functionalized" is meant to include functional groups attached to the surface of a nanostructure of the disclosure.

The nanostructures of the disclosure can optionally be functionalized by imprinting functional groups, such as antibodies, proteins, nucleic acids, and the like. Such nanostructures are particularly useful for molecular diagnostics and drug delivery. For example, to prolong or target analyte interaction with the hollow nanoparticle surface, a binding agent/targeting domain can be used to promote interaction of a nanostructure with a desired target.

In other embodiments, nanostructures of the disclosure are coated to inhibit the accumulation of biological material (e.g., proteinaceous agents) on the nanostructure's surface. In some embodiments, polyethyleneglycol (PEG) is immobilized on nanostructure surfaces to prevent nonspecific interactions.

Attached functional groups can comprise components for specifically, but reversibly or irreversibly, interacting with the specific analyte (e.g., can be labeled for site/molecule directed interactions). For example, a surface bound functional group (e.g., a targeting ligand) can be attached to a nanostructure of the disclosure. For example, a chemical molecule can be immobilized on the surfaces of a nanostructure of the disclosure.

A targeting ligand can include a receptor bound to the surface of a nanostructure of the disclosure that interacts reversibly or irreversibly with a specific analyte. Examples of functional groups (e.g., targeting ligands) include antigen-antibody pairs, receptor-ligand pairs, and carbohydrates and their binding partners. The binding ligand may be nucleic acid, when nucleic acid binding proteins are the targets. As will be appreciated by those in the art, the composition of the binding ligand will depend on the composition of the target analyte. Binding ligands to a wide variety of analytes are known or can be readily identified using known techniques.

For example, when the analyte is a single-stranded nucleic acid, the binding/targeting ligand is generally a substantially complementary nucleic acid. Similarly the analyte may be a nucleic acid binding protein and the capture binding ligand is either a single-stranded or double-stranded nucleic acid; alternatively, the binding ligand may be a nucleic acid binding protein when the analyte is a single or double-stranded nucleic acid. When the analyte is a protein, the binding ligands include proteins or small molecules. For example, when the analyte is an enzyme, suitable binding ligands include substrates, inhibitors, and other proteins that bind the enzyme, i.e. components of a multi-enzyme (or protein) complex. As will be appreciated by those in the art, any two molecules that will associate, may be used, either as the analyte or the functional group (e.g., targeting/binding ligand). Suitable analyte/binding ligand pairs include, but are not limited to, antibodies/antigens, receptors/ligand, proteins/nucleic acids; nucleic acids/nucleic acids, enzymes/substrates and/or inhibitors, carbohydrates (including glycoproteins and glycolipids)/lectins, carbohydrates and other binding partners, proteins/proteins; and protein/small molecules. In one embodiment, the binding ligands are portions (e.g., the extracellular portions) of cell surface receptors.

The disclosure provides nanostructures that have use in the detection of analytes in the environment, including explosive and biological agents as well as in vivo. Accordingly, the invention is useful in Homeland Security and the military for detection of analytes as well as for medical diagnostics. In one embodiment, the disclosure provides kits for monitoring military personnel in a war situation where they may be exposed to toxins. The nanostructures are administered or contacted with the subject prior to potential exposure. The subjects can then be monitored at set intervals using a detection device.

Commercial applications include environmental toxicology, materials quality control, food and agricultural products monitoring, anesthetic detection, automobile oil or radiator fluid monitoring, hazardous spill identification, medical diagnostics, detection and classification of bacteria and microorganisms both in vitro and in vivo for biomedical uses and medical diagnostic uses, infectious disease detection, body fluids analysis, drug discovery, telesurgery, illegal substance detection and identification, and the like.

Applications for the nucleic acid constructs provided herein include selective treatment of cancer, viral infection, genetic diseases, nucleic acid delivery for research and the like.

Provided herein are hollow nanospheres than can be used for the delivery of biological agents to a cell in vitro or in vivo. The biological agent can be a nucleic acid (e.g., a polynucleotide, oligonucleotide, peptide or polypeptide). In one aspect, a nucleic acid of interest is conjugated or operably linked to a hollow nanosphere of the disclosure.

An isolated nucleic acid construct refers to an oligonucleotide or polynucleotide associated with a hollow nanopshere of the disclosure. For example, a nucleic acid construct includes, but is not limited to, an oligonucleotide or polynucleotide associated with hollow silica nanopshere as described herein either directly or via a functional linker. An oligonucleotide or polynucleotide in the nucleic acid constructs of the disclosure include fusion polypeptides or peptides, chemical moieties that reduce the net anionic charge of an oligonucleotide or polynucleotide and combinations thereof.

The term polynucleotide(s) and oligonucleotide(s) generally refers to any polyribonucleotide or polydeoxyribonucleotide, which may be unmodified RNA or DNA or modified RNA or DNA. Thus, for instance, an oligonucleotide as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. Thus, a oligonucleotide can comprise an siRNA, an antisense molecule, a ribozyme and the like. For example, in one aspect of the disclosure the siRNA can comprise (fomivirsen) an antisense drug to treat a condition called cytomegalovirus (CMV) retinitis. Other suitable siRNA molecules will be apparent to those of skill in the art. Furthermore, it will be recognized that expression vectors or gene delivery constructions comprising DNA, RNA, a combination of DNA and RNA, and vectors or constructs comprising nucleic acid analogs can be adsorbed to the hollow silica nanospheres of the disclosure. The vector or construct can comprise any of a large number of therapeutic, diagnostic or research genetic sequences encoding enzymes, inhibitors, antisense, siRNA, ribozymes, and therapeutic proteins known in the art, such molecules are known or easily identified in the art (e.g., GFP, growth factors, enzymes, soluble domains of receptor ligands and the like).

In addition, a polynucleotide or oligonucleotides also includes triple-stranded regions comprising RNA or DNA or both RNA and DNA. The strands in such regions may be from the same molecule or from different molecules. The regions may include all of one or more of the molecules, but more typically involve only a region of some of the molecules.

In some aspects a polynucleotide or oligonucleotide includes DNAs or RNAs as described above that contain one or more modified bases. Thus, DNAs or RNAs with backbones comprising unusual bases, such as inosine, or modified bases, such as tritylated bases, are polynucleotides or oligonucleotides as the term is used herein.

As used herein, a nucleic acid domain, used interchangeably with oligonucleotide or polynucleotide domain, can be any oligonucleotide or polynucleotide (e.g., a ribozyme, antisense molecule, polynucleotide, oligonucleotide and the like). Oligonucleotides or polynucleotides generally contain phosphodiester bonds, although in some cases, nucleic acid analogs are included that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g. to increase the stability and half-life of such molecules in physiological environments. Mixtures of naturally occurring nucleic acids and analogs are encompassed by the term oligonucleotide and polynucleotide; alternatively, mixtures of different nucleic acid analogs, and mixtures of naturally occurring nucleic acids and analogs can be made. Furthermore, hybrids of RNN, RNB, DNA, and RNA can be used. dsDNA, ssDNA, dsRNA, siRNA are encompassed by the term oligonucleotide and polynucleotide.

A polynucleotide refers to a polymeric compound made up of any number of covalently bonded nucleotide monomers, including nucleic acid molecules such as DNA and RNA molecules, including single-double- and triple-stranded such molecules, and is expressly intended to embrace that group of polynucleotides commonly referred to as "oligonucleotides", which are typically distinguished as having a relatively small number (no more than about 30, e.g., about 5-10, 10-20 or 20-30) of nucleotide constituents.

As used herein, the term "siRNA" is an abbreviation for "short interfering RNA", also sometimes known as "small interfering RNA" or "silencing RNA", and refers to a class of about 19-25 nucleotide-long double-stranded ribonucleic acid molecules that in eukaryotes are involved in the RNA interference (RNAi) pathway that results in post-transcriptional, sequence-specific gene silencing.

The term "dsRNA" is an abbreviation for "double-stranded RNA" and as used herein refers to a ribonucleic acid molecule having two complementary RNA strands and which stands distinct from siRNA in being at least about 26 nucleotides in length, and more typically is at least about 50 to about 100 nucleotides in length.

As described above, the nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g. the individual units of a peptide nucleic acid, each containing a base, are referred to herein as a nucleoside.

The nucleic acid domain of a nucleic acid construct described herein is not limited by any particular sequence. Any number of oligonucleotide or polynucleotides useful for diagnostics, therapeutics and research can be used in the methods and compositions of the disclosure. Various sources of oligonucleotides and polynucleotides are available to one of skill in the art. For example, fragments of a genome may be isolated and the isolated polynucleotides modified in accordance with the disclosure to reduce the overall net anionic charge using phosphodiester and/or phosphothioate protecting groups or may be used as a source for extension of the oligonucleotide or polynucleotide using, for example, nucleic acid synthesis techniques known in the art.

Delivery of a polynucleotide can be achieved by introducing the polynucleotide into a cell using a hollow nanosphere of the disclosure. For example, a construct comprising such a polynucleotide can be delivered into a cell using a colloidal dispersion of hollow nanospheres. Alternatively, a polynucleotide construct can be incorporated (i.e., cloned) into an appropriate vector which is then linked to the nanosphere. For purposes of expression, the polynucleotide encoding a fusion polypeptide may be inserted into a recombinant expression vector. The expression vector typically contains an origin of replication, a promoter, as well as specific genes that allow phenotypic selection of the transformed cells. Vectors suitable for such use include, but are not limited to, the T7-based expression vector for expression in bacteria (Rosenberg et al., Gene, 56:125, 1987), the pMSXND expression vector for expression in mammalian cells (Lee and Nathans, J. Biol. Chem., 263:3521, 1988), baculovirus-derived vectors for expression in insect cells, cauliflower mosaic virus, CaMV, and tobacco mosaic virus, TMV, for expression in plants.

Depending on the vector utilized, any of a number of suitable transcription and translation elements (regulatory sequences), including constitutive and inducible promoters, transcription enhancer elements, transcription terminators, and the like may be used in the expression vector (see, e.g., Bitter et al., Methods in Enzymology, 153:516-544, 1987). These elements are well known to one of skill in the art.

The term "operably linked" and "operably associated" are used interchangeably herein to broadly refer to a chemical or physical coupling of two otherwise distinct domains that each have independent biological function. For example, operably linked refers to the functional linkage between a regulatory sequence and the polynucleotide regulated by the regulatory sequence. In another aspect, operably linked refers to the association of a nucleic acid domain and a transduction domain such that each domain retains its independent biological activity under appropriate conditions. Operably linked further refers to the link between encoded domains of the fusion polypeptides such that each domain is linked in-frame to give rise to the desired polypeptide sequence.

Nanoparticles can serve as a delivery platform that allows for "attachment" of DC-stimuli and antigen on the same particles, which can then be used for induction of immune responses. Silica-NPs appear to have the lowest toxicity compared to other nanomaterials tested.

The nanostructures of the disclosure can be used in vivo and in vitro to detect, deliver, identify, and/or characterize analytes of interest. The nanostructures can be used to detect analytes in environmental samples as well as samples derived from living organisms. As used herein, the term "sample" is used in its broadest sense. For example, a sample can comprise a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. The nanostructures can be used, for example, in bodily fluids in vivo or in vitro. Such bodily fluids include, but are not limited to, blood, serum, lymph, cerebral spinal fluid, aqueous humor, interstitial fluid, and urine.

Introduction of plasmid DNA into cells for gene expression is being widely used in biology. Primary cells like dendritic cells are very difficult to transfect using methods like lipofection that work very well for cell lines. Electroporation using a specialized machine and reagents has been commercialized (Amaxa biosystems) and it is currently, next to viral vectors, the best method on the market for introduction of plasmid DNA into dendritic cells. This application uses electric force to introduce DNA into DCs; however, this method causes a high number of cell death. And gene expression peaks at 20 h, and at 48 h nearly 30% of the cells are dead and gene expression is reduced to 10% of the cells.

Since immature DCs readily take up particles, the methods and compositions of the disclosure have taken advantage of DCs natural function and utilized nanoparticles coated with DNA as a "Trojan horse" to deliver nucleic acids into DCs. In vivo, DCs need to encounter both the antigen and a DC stimulus for optimal induction of antitumor Cytotoxic T lymphocytes (CTL) responses. DCs that encounter antigen without stimulus can induce immune tolerance, since DCs effectively take up particles. The disclosure generates multi-functional silica-NPs that carry antigen-encoding nucleic acids and the DC stimulus to ensure the generation of strong anti-tumor immune responses. Coupling of nucleic acids and an immunostimulatory agent or peptide (e.g., Hp-91) on silica-NPs improves the efficacy of these multifunctional nanoparticles. Such compositions and methods are demonstrated in the non-limiting examples below which demonstrate in vitro assays for DC uptake, activation, and CTL induction and in vivo using a mouse melanoma model.

Figure 6:
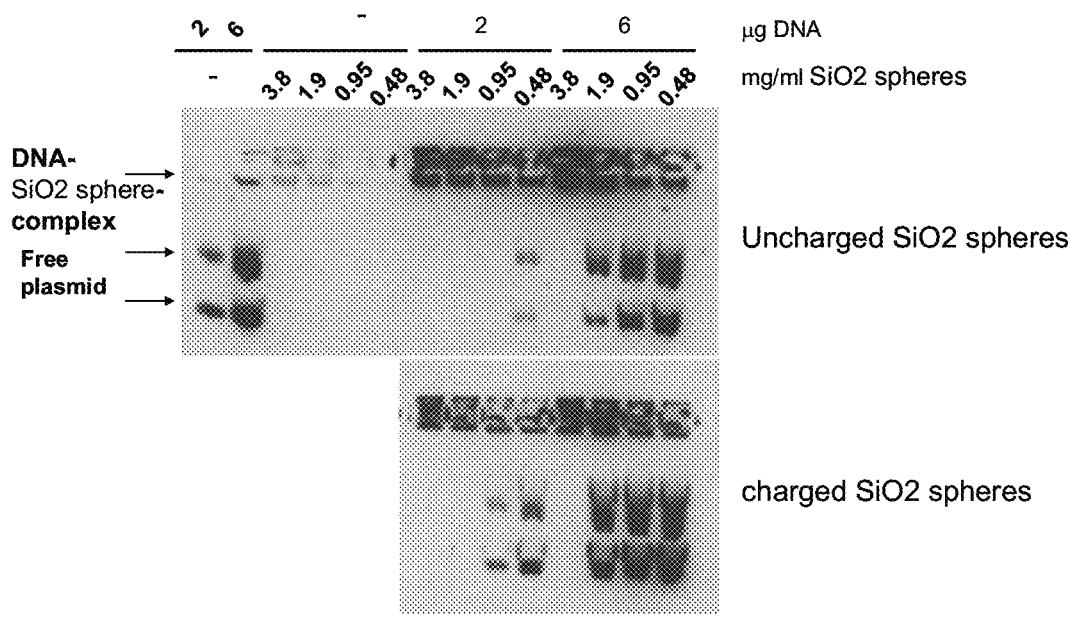
FIG. 6 is a photograph of DNA adsorbed to hollow silica spheres. 2 μg or 6 μg plasmid DNA were complexed with different amounts (0.48-3.8 mg/ml) of either uncharged (top panel) or charged (bottom panel) silica spheres. Plasmid only, silica spheres only, as well as the complexes were resolved on a 1% agarose gel at 100V for 1 h. (Geldoc used for image).

To adsorb a oligo- or poly-nucleotide to hollow $SiO_2$ spheres, the spheres are resuspended in and appropriate media. In one aspect, the sphere are resuspended in PBS and sonicated for 15 min to several hours at a setting sufficient enough to resuspend the spheres. The resuspended spheres are then diluted and mixed with the desired nucleic acid molecules. For example, different amounts of $SiO_2$ spheres were diluted in 700 mM NaCl and 100 µl of the dilution was mixed at 10 µl per minute with 100 µl of a plasmid dilution under constant vortexing. Adsorbed nucleic acids can be identified or purified by filtration or separation. For example, adsorbed nucleic acids was resolved on an agarose gel after formation of the complexes (FIG. 6). Adsorption of the nucleic acids to the $SiO_2$ spheres prevents the DNA from running into the gel and instead it stays in the wells with the $SiO_2$ spheres, whereas free unbound plasmid will run as two bands. Uncharged (defined as 100 nm silica spheres with the polystyrene core removed by solvent extraction) and charged (defined as the 100 nm silica spheres with the polystyrene core removed by solvent extraction, but containing surface amino group by treatment with $(MeO)_2Si(CH_2)_2NH_2$) $SiO_2$ spheres were compared. Uncharged $SiO_2$ spheres were more effective at adsorbing plasmid DNA. For example, at 0.95 mg/ml the uncharged $SiO_2$ spheres adsorbed all of the 2 µg DNA, whereas twice the amount of charged $SiO_2$ spheres was required to adsorb the same amount of DNA.

Figure 7:
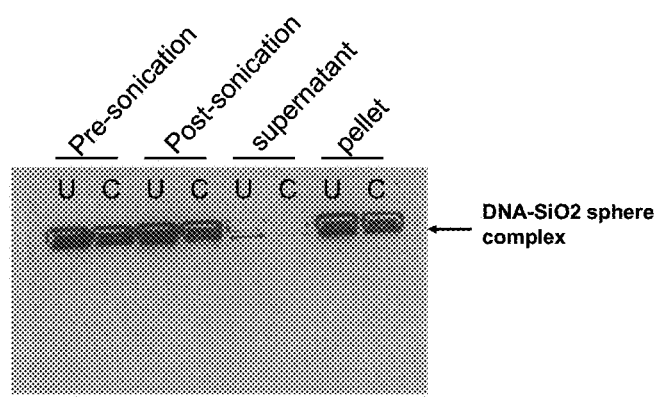
FIG. 7 is a photograph of DNA adsorbed to hollow silica spheres: testing DNA-silica sphere complex stability. Aliquots from each step of the buffer exchange procedure were collected and resolved on a 1% agarose gel at 100V for 1 h. U=uncharged silica spheres and C=charged silica sphere-DNA complexes.

To evaluate uptake of $SiO_2$ sphere-DNA complexes by primary human dendritic cells (DCs), the $SiO_2$ spheres-DNA complexes were sonicated briefly for 15 min at high, spun down at 6000 rpm for 10 minutes, and the pellet was resuspended in culture media. To test whether the plasmid would disassociate from the $SiO_2$ spheres, aliquots were taken before sonication, post sonication, from the supernatant after the spin, and from the resuspended pellet (FIG. 7). At all stages the plasmid DNA was retained in the wells, indicating that neither the sonication nor the spinning caused the plasmid DNA to disassociate from the $SiO_2$ spheres. The same was true for charged and uncharged $SiO_2$ spheres.

Figure 8:
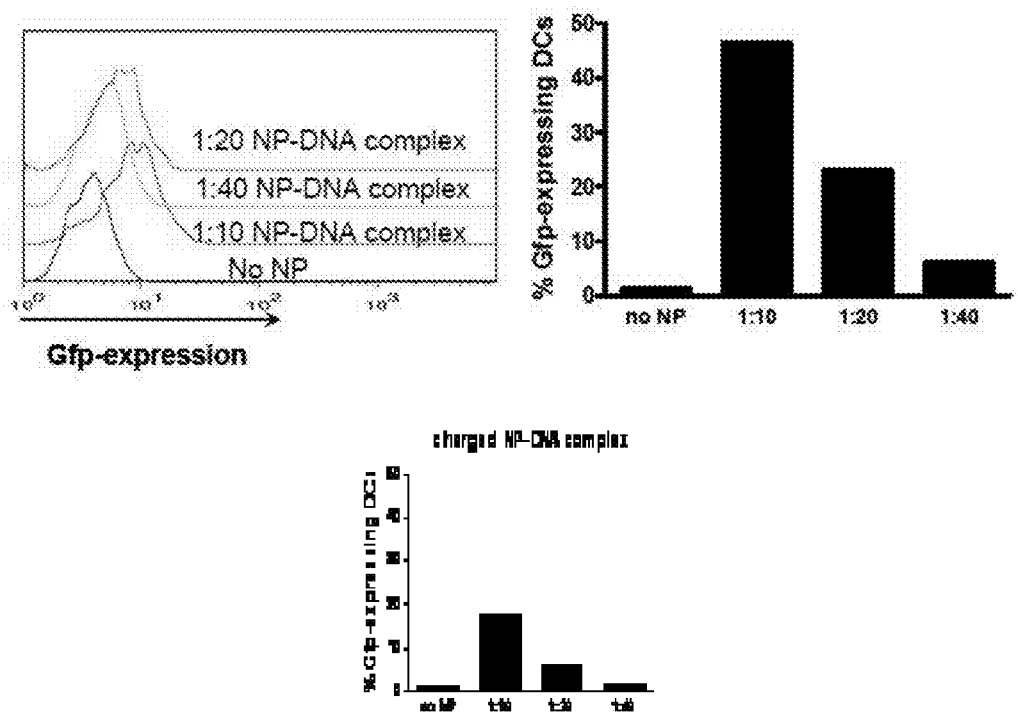
FIG. 8 shows GFP-expression in silica sphere-DNA complex transfected DCs. Immature human DCs were exposed to different dilutions of the silica sphere-DNA complexes. 48 h later Gfp expression was measured by flow cytometry gated on live cells. The histograms depict the relative fluorescence intensity at the different dilutions of charged silica sphere-DNA complexes added to the DCs. B) Percentage of DCs expressing Gfp at 48 h after exposure to different dilutions of charged silica sphere-DNA complexes or uncharged silica sphere-DNA complexes.

Since the plasmid DNA-$SiO_2$ sphere complexes and was maintained during exchange of high salt to culture media, examination of whether immature human DCs would take up the complexes and express the transgene was analyzed. A plasmid that encodes for gfp was used, because it allows for easy monitoring of GFP expression by flow cytometry. $10^5$ immature DCs were exposed to 25 µl diluted $SiO_2$ sphere-DNA complexes for 2 h and subsequently 1 ml of fresh medium was added to the cells. DCs were collected 48 h after exposure to the complexes. At 1:10 dilution of the charged $SiO_2$ sphere-DNA complex (0.075 ug plasmid DNA per $10^5$ cells), a strong shift in mean fluorescence intensity was observed and 45% of the DCs expressed GFP (FIG. 8). The uncharged $SiO_2$ sphere-DNA complexes at the same dilution showed approximately 2-fold lower percentage of Gfp-positive DCs, which correlated with the fact that ~2-fold less plasmid was adsorbed to the same number of particles charged $SiO_2$ spheres (see FIG. 6). Using the "state of the art" transfection method for DCs, the Amaxa system, which is electroporation with a specialized machine, only 10-15% of the DCs expressed GFP at 48 h when 0.5 µg plasmid DNA were used per $10^5$ cells, which is 6.6-fold more DNA and the percentage of cells expressing GFP is 3-fold lower. Thus the $SiO_2$ spheres provide a very powerful tool to introduce a transgene into DCs.

A nanostructure of the disclosure can be formulated with a pharmaceutically acceptable carrier, although the nanostructure may be administered alone, as a pharmaceutical composition.

A pharmaceutical composition according to the disclosure can be prepared to include a nanostructure of the disclosure, into a form suitable for administration to a subject using carriers, excipients, and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, anti-oxidants, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.).

The pharmaceutical compositions according to the disclosure may be administered locally or systemically. By "effective dose" is meant the quantity of a nanostructure according to the disclosure to sufficiently provide measurable SERS signals. Amounts effective for this use will, of course, depend on the tissue and tissue depth, route of delivery and the like.

Typically, dosages used in vitro may provide useful guidance in the amounts useful for administration of the pharmaceutical composition, and animal models may be used to determine effective dosages for specific in vivo techniques. Various considerations are described, e.g., in Langer, Science, 249: 1527, (1990); Gilman et al. (eds.) (1990), each of which is herein incorporated by reference.

As used herein, "administering an effective amount" is intended to include methods of giving or applying a pharmaceutical composition of the disclosure to a subject that allow the composition to perform its intended function.

The pharmaceutical composition can be administered in a convenient manner, such as by injection (e.g., subcutaneous, intravenous, and the like), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. The composition will typically be sterile and fluid to the extent that easy syringability exists. Typically the composition will be stable under the conditions of manufacture and storage and preserved against the contaminating action of microorganisms, such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, for example, sugars, polyalcohols, such as mannitol, sorbitol, or sodium chloride are used in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the subject's diet. For oral administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit.

For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic in the amounts employed. In addition, the pharmaceutical composition can be incorporated into sustained-release preparations and formulations.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Supplementary active compounds can also be incorporated into the compositions.

The working examples provided below are to illustrate, not limit, the disclosure. Various parameters of the scientific methods employed in these examples are described in detail below and provide guidance for practicing the disclosure in general.

EXAMPLES

The disclosure demonstrates that a plasmid encoding for the green fluorescent protein (Gfp) can be used as a reporter to measure gene expression. This is a commonly used reporter-gene and it enables a fast and convenient readout of the number of cells that express the transgene by flow cytometry.

The data show that plasmid DNA can be absorbed onto hollow Silica-NPs of 45, 80, and 120 nm size. Surface modifications that increase the charge of the Silica-NPs are evaluated on all sizes to determine if the DNA adsorption can be increased. To add additional amine groups, the hollow Silica-NPs are functionalized with 3-aminopropyl(trimethoxy)silane. For example 1 mg of calcinated hollow silica spheres, prepared from the 100 nm templates, are suspended in 2 mL of 1% 3-aminopropyl(trimethoxy)silane acetone solution. The mixture are stirred slowly for 2 hours with a magnetic stirrer followed by collecting the particles by centrifugation. The collected particles are washed with ethanol and dried in vacuum for 24 hours at room temperature. Subsequently the particles are heated at 450° C. Surface modification by adding poly-L-lysine are performed after the calcination process by briefly incubating the particles in a 0.1% poly-L-lysine solution. The solution phase size distribution of the nanoparticles also are routinely monitored by dynamic light scattering (DLS) measurements. This will give information on the dispersal state of the nanoparticles just before their use in biological experiments. As shown in the data different amounts of plasmid DNA are adsorbed to titrated amounts of the different NPs to compare the efficacy of complex formation and to identify the most effective silica-NP for DNA adsorption. The complexes are resolved on a 1% agarose gel.

Gene expression: Once the optimal silica-NP surface modification is determined, DNA is adsorbed to different sizes of the NP (45, 80, and 120 nm) to determine which size confers the strongest transgene expression. The rationale to compare different sizes is that they could traffic differently, for example it is possible that more of the smaller NPs translocate to the nucleus. Immature human DCs are incubated with increasing doses of the DNA-NP complexes as described in data using a plasmid that encodes for gfp. 48 h after exposure to the DNA-NP complexes, Gfp expression are analyzed by flow cytometry. Kinetics of transgene expression as well as cell viability using propidium iodide staining are determined by flow cytometry.

Peptide conjugation: To identify which surface modification is best suited for peptide conjugation, fluorescently labeled peptides (FITC on the N-terminus) are conjugated to the different aminefunctionalized silica-NPs. The free C-terminus of the peptide will form an amide bond with the amino groups on the silica-NPs using EDAC as the coupling reagent. Only for the purpose of demonstrating peptide binding to these surfaces will 1 µm size silica-NPs be used, as this allows for visualization and quantification of the bound peptide by microscopy. Once the most effective silica-NP modification for DNA and peptide binding is identified, binding of peptides and DNA to the same 1 µm size silica-NPs is assessed. To determine co-localization FITC labeled peptide and tetramethyl-rhodaminelabeled-plasmid DNA are used and analyzed by microscopy. Additionally adsorption of DNA to peptide conjugated silica-NPs of different sizes by gel electrophoresis and zeta potential measurements are taken. After demonstrating peptide and DNA binding to the same particle by microscopy, the same methods are used to generate smaller size multi-functional NPs (45, 80, and 120 nm) for the experiments listed below.

Generation of dendritic cells: To generate human DCs, anonymous Buffy coats from healthy donors are purchased from the San Diego Blood bank. DCs are prepared from peripheral blood monocytes by culturing CD14+ monocytes in GM-CSF and IL-4 for 5 to 7 days, at which point they are immature DCs. To generate mouse DCs, bone marrow-derived dendritic cells (BM-DC) are prepared from C57/BL6 mice. Briefly, single bone marrow cell suspensions are obtained from femurs and tibias, and then depleted of lymphocytes, granulocytes, and Ia+ cells using a mixture of monoclonal antibodies (anti-CD4, anti-CD8, anti-B220/CD45R, and anti-Ia) for 45 minutes on ice, followed by incubation with low-toxicity rabbit complement for 30 minutes at 37° C. Cells are resuspended at a concentration of $10^6$ cells/ml in medium supplemented with recombinant murine GM-CSF (10 ng/ml) and plated at 3 ml/well in 6-well plates. Floating cells are removed on days 3 and 5 of culture by gentle pipetting and fed with fresh medium. On day 7, the non-adherent and slightly adherent cells are collected for the experiments. Further purification are achieved by positively selecting CD11c+ cells using magnetic beads.

Testing activity of peptide-NP complexes: After demonstrating Hp-91 peptide binding to the NPs by microscopy, the DC-stimulatory function of the NP-bound peptides are evaluated on both mouse and human DCs. During the maturation process DCs up-regulate co-stimulatory and adhesion molecules and secrete large amounts of inflammatory cytokines. Therefore, DC maturation can easily be measured by flow cytometry looking at surface molecule expression levels by ELISA measuring the amount of secreted cytokines.

The immature human and mouse DCs are exposed to increasing doses of silica-NP-Hp-91 complex, non-complexed silica-NP (negative control), free Hp-91 peptide, or LPS as positive controls. Cell culture supernatants are analyzed for the presence of inflammatory cytokines by ELISA and changes in cell surface molecule expression are monitored by flow cytometry. The same assays are used to determine the extent to which CD40L plasmid DNA adsorbed to hollow silica-NPs confers DC maturation.

Intracellular trafficking of the silica-NPs: If different size silica-NPs confer different potentials for gene expression, intracellular trafficking of the silica-NPs are analyze to determine a possible mechanism. DCs are exposed to FITC-labeled NPs of different sizes and harvested at different time points (30 min, 1 h, 2 h, 6, and 24 h) after exposure to the NPs. Cells are spun onto glass slides and stained with Hoechst to visualize the nucleus and determine the localization of particles in the nucleus. Cells are stained with lysotracker (Molecular probes), which labels endosomes and lysosomes as well as with an anti-LAMP1 antibody, which reacts with a lysosomal protein. These experiments shed light on whether particles of certain sizes or modifications get stuck in lysosomes or whether they translocate to the nucleus. Furthermore, to determine whether the NPs and DNA traffic together within the cell or whether in certain intracellular milieus the DNA is released from the NPs, tetramethyl-rhodamine-labeled-plasmid DNA are adsorbed to FITC-labeled NPs and intracellular trafficking kinetics are monitored by microscopy.

A higher density of positive charge on the NP surface is expected to cause higher amounts of DNA adsorption. Thus, the NPs with extra amine groups or with added poly-L-lysine adsorbed on the surface are expected to bind more DNA. If both the DC-stimulatory peptide and the CD40L plasmid confer similar DCs maturation capacity.

2 plasmids can also be adsorbed to the NPs, one encoding the melanoma antigen and the other encoding CD40L as the DC stimulatory molecule. Alternatively non-methylated CpG oligonucleotides, which are also strong stimuli for DC activation, are adsorbed to the NPs.

A MART1 (=melanoma antigen)-expressing plasmid and a human MART1-specific CD8+ T cell clone are used to evaluate the induction of antimelanoma CTL responses. The size and surface modification of Silica-NPs that enabled the most potent gene expression for human DCs is used to adsorb a MART1-encoding plasmid and to covalently attach the DC-stimulatory peptide Hp-91. Immature human DCs are exposed to increasing doses of Silica-NP-complexes or non-complexed NPs as control and subsequently cocultured with a CD8+ MART1-specific T cell clone. T cell activation will be measured by IFN-γ and granzymeB ELISPOT as well as in CTL assays.

Using the B16-OVA melanoma tumor model, multi-functional silica-NPs carrying the OVA plasmid (as surrogate tumor antigen) and Hp-91 are injected into mice before injection of B16-OVA tumor cells to measure the prophylactic effect. To measure their therapeutic potential, the complexes will be injected into tumor bearing mice. In both settings the immunized mice are monitored for the development of anti-OVA immune responses and for tumor growth.

Human monocyte-derived DCs, for example, were generated from PBMCs isolated from healthy donors by culturing adherent cells in GM-CSF and IL-4 for 5 to 7 days. $SiO_2$ nanoparticles were generated using polymer beads as template and the surface was functionalized with amino silane or amino phosphoric acid and the polymer core was removed by calcination or organic solvents. Several nanoparticles were synthesized: with non-modified surfaces, functionalized with amine groups, or functionalized with poly-L-lysine (pLL). DNA adsorption to the NPs was determined by gel electrophoresis. DNA adsorption to the NPs caused the DNA to be retained in the well, whereas unbound DNA migrated into the gel. NP uptake by DCs: DCs were incubated with NPs for 2 h in a 50 ul at 37° C. Subsequently fresh media was added to the cells and gene expression was analyzed 48 h later. Using these methods the data indicated that silica-NPs can adsorb plasmid DNA. Surface modifications including amine groups and poly-L-lysine (pLL) that introduced additional positive charges were tested and lead to increased DNA adsorption to the NPs. Furthermore, DNA could be adsorbed to silica-NPs of different sizes (45, 80, and 120 nm).

To test uptake, immature DCs were exposed to FITC-labeled NPs of 45, 100, and 200 nm diameter. All sizes were effectively taken up by DCs and no obvious preference was observed. Both unmodified and amine-modified NPs were taken up by DCs, but pLL-modified NPs were not. Although the NPs were found predominantly in the cytoplasm, confocal microscopy indicated that NPs were also present in the nucleus of the DC. DCs loaded with NPs showed high viability for at least 7 days, showing low toxicity compared to other transfection methods. A plasmid that encodes for gfp was used to demonstrate uptake by cells. The plasmid was adsorbed to the 120 nm non-modified or amine modified-NPs. Immature DCs were exposed to NP-DNA complexes and analyzed for Gfp expression by flow cytometry. Using DNA complexes with amine modified NPs 45% of the DCs expressed GFP at 48 h. DNA complexes with un-modified NPs showed 50% reduced Gfp expression, which also correlated with the fact that ~50% less DNA was adsorbed. In contrast to electroporation methods, no death of DCs and ~6-fold increase in the percentage of transfected DCs was observed at 48 h.

These experiments demonstrate that $SiO_2$— nanoparticles of 80 and 120 nm are more efficient than electroporation to introduce a transgene into DCs in vitro and possibly in vivo.

The data show that human immature DCs take up Silica-NP-DNA complexes and express the transgene at 48 h. A MART1 (=melanoma antigen)-expressing plasmid and a MART1-specific CD8+ T cell clone are used to evaluate the induction of human anti-melanoma CTL responses in vitro.

IFN-γ ELISPOT: Hollow silica-NPs are adsorbed with MART1-encoding plasmid (Silica-NP-MART1=negative control), CD40L encoding plasmid (Silica-NP-CD40L=negative control), both plasmids (Silica-NP-MART1/CD40L=new vaccine), the DC-stimulatory peptide Hp-91 (Silica-NP-Hp-91=negative control), and MART1-encoding plasmid plus Hp-91 (Silica-NP-MART1/Hp-91=new vaccine). Immature human DC are incubated for 2 hours with the NP-DNA complexes and respective controls listed above. 48 h and 72 h after NP exposure the DCs are co-cultured with a CD8+ MART1-specific T cell clone for 24 h. As a positive control for T cell activation, the immature DCs are exposed to LPS for 48 h and then pulsed with MART1 peptide (ELAGIGILTV). T cell activation are measured by IFN-γ ELISPOT, which detects and quantified the number of IFN-γ secreting cells used as indication for T cell activation.

CTL assay: Immature human DC are incubated for 2 hours with the NP-DNA complexes and respective controls listed above. 48 h and 72 h after NP exposure the DCs are co-cultured with a CD8+ MART1-specific T cell clone for 24 h. Subsequently the T cell clone are evaluated for the ability to kill MART expressing target cells in a CTL assay. As target cells antigen processing-deficient HLA-A2.1+ T2 cells pulsed with the MART1 peptide (ELAGIGILTV) or irrelevant 9mer peptides as a control are used. Prior to peptide pulse, the target cells are labeled with the membrane dye PKH26 (red) and subsequently pulsed with 50 μg/ml peptide for 2 h. Cells are transferred ($10^4$) to round-bottom 96-well plates and varying numbers of CTLs are added. The co-cultures are incubated for 4 h at 37° C. At the end of the culture, the cell viability are determined based on the mitochondrial trans-membrane potential ($\Delta\cdot m$) using 3,3'-dihexyloxacarbocyanine iodine (DiOC6) by flow cytometry. Live cells are DiOC6-bright, whereas dying and dead cells are DiOC6-dim. OVA-specific killing of target cells are calculated by gating on the red target cells using the following equation: (% of DiOC6dim target cells pulsed with peptide)−(% of DiOC6dim target cells pulsed without peptide). In addition a Granzyme B ELISPOT assay are used to determine the cytolytic potential of the activated T cells. This assay has shown good correlation with Chromium release assays, but lacks the radioactive hazard.

DCs exposed to Silica-NP-MART1, Silica-NP-CD40L, or Silica-NP-Hp-91 are not expected to cause T cell activation. DCs exposed to the multi-functional Silica-NP-MART1/CD40L as well as the Silica-NP-MART1/Hp-91 are expected to cause strong T cell activation.

Common mouse melanoma model will be used, where the melanoma cell line B16-OVA are injected into mice. In this melanoma model, the tumor cells express ovalbumin (OVA), which serves as surrogate tumor antigen, allowing for the measurement of OVA-specific immune responses. Thus a plasmid encoding OVA is used.

The Silica-NP size and composition that confers the strongest T cell activation are used to generate multi-functional NPs containing plasmid DNA that encodes for chicken ovalbumin (OVA), together with CD40L plasmid or DC-stimulatory peptides. The multi-functional NPs are evaluated in the in vivo model below in both a prophylactic and therapeutic setting. Most vaccines using "naked" DNA have shown promising results when injected i.m. Since the goal is to target DCs, which is more likely to be achieved by i.d. injection, the potency of the vaccines is compared when given i.d. or i.m. The potency and type of immune responses has been shown to correlate with protection from tumor growth and tumor rejection. Therefore, the development of an immune responses as well as tumor growth are measured in both the prophylactic and therapeutic setting.

It is generally believed that for tumor rejection strong Th1 immune responses characterized by CD8 T cells secreting IFN-γ are required, whereas a Th2 response is thought to play a lesser role. In order to gain a better understanding of the tumor rejection mechanism cause by the multi-functional silica-NP vaccine, further characterization of the type of immune response is performed. In mouse, the production of antibody isotypes can be used as a surrogate measurement for the type of immune response. IgG2a is recognized as characteristic of a Th1 response, whereas the production of IgG1 is characteristic of a Th2 response. Therefore, the assessment of the type of immune response are done by measuring IgG1, IgG2a and IgG2b levels by ELISA. The ratio of IgG2a/IgG1 antibody titers are used as indicator of Th bias. Furthermore, the secretion of cytokines also defines the type of immune response. A Th2 response is characterized by the secretion of Th2 type cytokines, such as IL-4, IL-5, whereas a Th1 type response is characterized by the secretion of IL-2 and IFN-γ.

IL-10 and TGF-β are cytokines that contribute to regulatory T cell responses, which interfere with tumor rejection. Therefore, the secretion of these cytokines are measured by ELISA as well.

Prophylaxis: Groups of mice will receive the multi-functional silica NP vaccine first and then receive injections of B16-OVA tumor cells. Half the mice from each group are sacrificed to measure immune responses and the other half are monitored for tumor growth. Groups of mice will receive i.d. or i.m. injections of PBS, Silica-NP without DNA (neg. control), Silica-NP with irrelevant DNA encoding for a non-mammalian antigen e.g. firefly-luciferase (neg. control), Silica-NP-OVA/CD40L, Silica-NP-OVA-Hp91, Silica-NP-OVA, Silica-NP-CD40L, and Silica-NP-Hp91. Two doses of DNA 10 µg and 50 µg are evaluated either adsorbed to NPs or as "naked" DNA. 10 µg OVA protein in IFA are injected as positive control. 7-14 days after the first injection, mice will receive a booster injection identical to the first injection. 10-14 days after the last immunization, half of the mice from each group will receive s.c. injections of $1 \times 10^5$ B16-OVA tumor cells and the other half are sacrificed to measure the development of immune responses (see below). The remaining mice are observed bi-weekly for tumor appearance by palpitation. As primary measurement, the time to tumor appearance in the treated groups compared to the PBS control is monitored. As secondary measurement of tumor size using a set of calipers is used. Tumors of at least 3 mm are scored. Mice are sacrificed if tumors reach 1.5 cm in diameter or at week 6 after injection of tumor cells, at which point all non-treated mice will have developed tumors.

Therapeutic: Mice will receive s.c. injections of $5 \times 10^5$ B16-OVA tumor cells. Once the tumor reaches 3 mm in size, mice will receive the same i.m. and i.d. injections of the multi-functional silica NPs and controls as listed above. In both settings, mice are divided randomly into groups (n=10) and, as above, half the mice from each group are sacrificed 10-14 days after the final injection to measure the development of immune responses and the other half are monitored for tumor growth. To measure the development of immune memory, mice that show complete rejection of the tumor, are challenged with a second injection of $5 \times 10^5$ B16-OVA cells 1 month after the final injection of multifunctional silica NPs.

Measurement of immune response: Groups of mice will receive i.m. or i.d. injections as above. The in vivo induced T cell responses are detected in vitro using a variety of assays. 1) Proliferation assays are performed by adding OVA257-264 peptides (to stimulate CD8 T cells) and OVA323-339 (to stimulate CD4 T cells), PBS/no peptide (negative control) or ConA (positive control) to unseparated splenocytes, which contain T cells and antigen presenting cells, and measuring the uptake of [3H]-thymidine after 4 d. 2) Cytokine secretion: To measure T cell responses, unseparated splenocytes are set up as described above but the positive control are phorbal myristate acetate (PMA) and soluble anti-CD3, since ConA is not a very potent stimulus for Th2 cytokines. After 24 h, the culture supernatants are assessed for IL-4, IL-2, IL-5, IL-10, TGF-β and IFN-γ levels by ELISA. Furthermore, IFN-γ ELISPOT are used to measure the number of cytokine secreting T cells. To further investigate the contribution of CD8+ and CD4+ T cells to the cytokine secretion, either cell type are depleted from the splenocytes using specific antibodies, prior to in vitro culture. 3) CTL assays: To expand OVA-specific T cells from the spleens of the immunized mice, the splenocytes are cultured in 24-well plates for 6 days at a concentration of $3 \times 10^6$ cells in 1.0 ml of medium with the addition of recombinant mouse IL-2 (50 units/ml) after 24 h of culture. Furthermore, a standard LDH release assay are performed at day 6 to measure cytolytic activity, by incubating the splenocytes with target cells pulsed with and without OVA peptide. The absorbance values from supernatants are recorded at OD 490 nm. The percent of specific lysis are calculated as follows: (DExp.−ODSpon.E−ODSpon.T/ODMax.T.−ODSpon.T)× 100, where ODExp. is the OD related to the experimental LDH relase, ODSpon.E. is the OD related to the spontaneous release of LDH from the effector cells only, ODSpon.T is the OD related to the spontaneous LDH release from target cells only, and ODMaxT. is the OD related to the maximum LDH release from target cells using lysis buffer.

In vivo immune response: To measure the immune responses directly in vivo, transfer of $2 \times 10^6$ OTI CD8+ T cells into the mice is performed one day prior to immunization with the silica-NP vaccines. These OTI CD8+ T cells are harvested from a T cell receptor transgenic mouse (B6 background) which are specific for Kb-SIINFEKL of OVA. Prior to injection, OT-I cells are labeled with Carboxyfluorescein succinimidyl ester (CFSE), which consists of a fluorescent molecule that stains the plasma membrane. During each round of cell division, relative fluorescence intensity of the dye is decreased by half, allowing us to examine cell division in vivo. 3 days after injection of OT-cells, the animals are tested for proliferation of OT-I cells by flow cytometry.

Toxicity: To monitor for potential pathological effects of the silica-NP vaccines, the spleen, liver and kidney are collected at time of euthanasia. The organs are weighed and additional tissue analysis are performed.

Mice that are immunized with DNA-NP-Hp-91-complexes are protected from tumor growth and reject the established tumor cells.

The effectiveness of the new silica-NP complexes in inducing melanoma-specific CTL are determined on a quantitative basis as follows: a). In vitro experiments: The target cells are incubated with decreasing concentrations of the OVA-derived peptides or corresponding nanoparticle based vaccines. Values obtained from the LDH-release assays and ELISPOT assays are used to construct dose-response curves and these are compared. IC50 values from a minimum of 5 independent experiments are compared for statistical significance using the Student t test. b).

Example 1

Preparation of the solution of hydrolyzed tetramethoxysilane. 14.0 mL tetramethoxysilane is added to 100 mL 0.01 M hydrochloric acid. The mixture is stirred at room temperature for 15 minutes. The solution is to be used as the precursor to deposit silica shells directly.

Example 2

Synthesis of core-shell silica spheres with 100 nm amine polystyrene beads. 4.0 mL of 2.6% w/v 100 nm sized amine polystyrene beads, 16 mL of 0.1% poly-L-lysine solution and 75 mL of 0.1 M phosphate buffer are mixed in a 150 mL pear-shaped flask. 2 mL of hydrolyzed tetramethoxysilane is added and the mixture is stirred vigorously with a vortex agitator at a speed of 3000 rpm. The stirring lasts 5 minutes at room temperature and the mixture is transferred into two 50 mL centrifuge tubes. A white precipitate is collected by centrifugation. The core-shell particles are suspended in deionized water and stirred with the vortex agitator for 5 minutes and then spun down again by centrifugation. The washing procedure is repeated one more time followed by washing with ethanol. 185 mg Core-shell particles are dried in vacuum at 60° C. for 48 hours.

Example 3

Synthesis of core-shell silica spheres with 200 nm amine polystyrene beads. The synthesis procedure is similar to example 2, except that the 100 nm amine polystyrene beads are replaced by 200 nm amine polystyrene beads.

Example 4

Synthesis of titania core-shell silica spheres with 200 nm amine polystyrene beads. 2.0 mL of 2.6% w/v 100 nm sized amine functionalized polystyrene beads and 80 mL of absolute ethanol are mixed in a 150 mL pear-shaped flask. 2.0 mL of 1 M titanium t-butoxide/ethanol solution is added and the mixture is stirred vigorously with a vortex agitator at a speed of 3000 rpm. The stirring lasts 2 minutes at room temperature and the mixture is transferred into two 50 mL centrifuge tubes. A white precipitate is collected by centrifugation. The core-shell particles are suspended in absolute ethanol and stirred with the vortex agitator for 5 minutes and then spun down again by centrifugation. The washing procedure is repeated one more. 120 mg Core-shell polystyrene/titania particles are dried in vacuum at 60° C. for 48 hours.

Example 5

Removing polymer cores by calcination. 10 mg of dry core-shell silica particles are placed in a furnace and the temperature is raised at a speed of 5° C./min to 450° C. The core-shell particles are calcinated in air at 450° C. for 4 hours and the temperature is then cooled at a speed of 5° C./min until it reaches room temperature. 3.2 mg of final product of hollow silica spheres is obtained as a white powder. Yield is nearly quantitative based on the number of template spheres.

Example 6

Removing polymer cores by dissolution in toluene. 10 mg of dried core-shell spheres are suspended in 20 mL of toluene and the mixture is stirred with a magnetic stirrer for 1 hour. The solid is collected by centrifugation. The washing procedure is repeated three more times followed by drying the particles in vacuum at 60° C. for 48 hours. 3.7 mg of hollow silica spheres is obtained as white powder. Some residual polystyrene is still evident from the infra-red spectra. The TEM photographs of this material show thicker shell walls, presumably from adsorbed polystyrene on the silica walls.

Example 7

Removing cores by dissolution with added ethylene diamine. 10 mg of dried core-shell spheres are suspended in a mixture of 5 mL of ethylene diamine and 15 mL dichloromethane and stirred with a magnetic stirrer for 1 hour. The solid is collected by centrifugation. The washing procedure is repeated three more times followed by drying the particles in vacuum at 60° C. for 48 hours. 3.5 mg of hollow silica spheres is obtained as white powder. Compared to Example 5 nearly all the polystyrene core is removed by this method.

Example 8

Functionalized the hollow silica spheres with 3-aminopropyl(trimethoxy)silane. 1 mg of calcined hollow silica spheres, prepared from the 100 nm templates, are suspended in 2 mL of 1% 3-aminopropyl(trimethoxy)silane acetone solution, The mixture is stirred slowly for 2 hours with a magnetic stirrer followed by collecting the particles by centrifugation. The collected particles are washed with ethanol and dried in vacuum for 24 hours at room temperature.

Table 1. Size of hollow silica spheres isolated and its dependence on the size of the templates and the methods of removing the polystyrene cores.

|  | Size of template (nm) | | |
| --- | --- | --- | --- |
|  | 100 | 200 | 500 |
| Diameter of core-shell spheres (nm) | 126± | 210 ± 6 | 454 ± 16 |
| Diameter of hollow spheres after calcinations (nm) | 126 ± 7 | 205 ± 7 | 443 ± 21 |
| Diameter of hollow spheres after dissolution (nm) | 102 ± 8 | 188 ± 9 | 397 ± 15 |

Example 9

Figure 9:
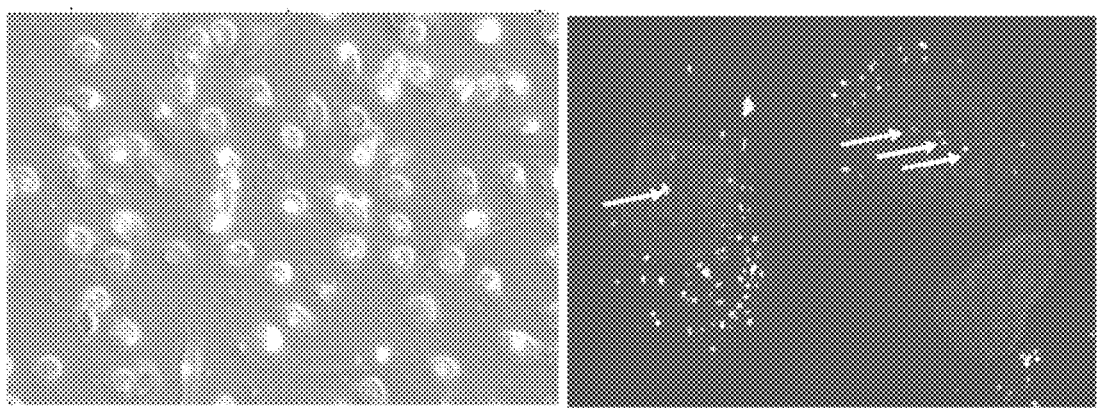
FIG. 9 shows a photomicrograph of uptake of Silica nanoparticles by dendritic cells. Immature human DCs were exposed to 200 nm FITC-labeled core-shell Silica-NPs. (left) 2 h after endocytosis, the cells were imaged in bright-field using an inverted fluorescence microscope (40× magnification). (right) 6 h after exposure, the nuclei were stained with Hoechst (blue) and the cells were imaged using a confocal microscope (60× magnification). The white arrows point to the location in the nucleus where nanoparticles were observed.

Uptake of silica-NPs by dendritic cells. Immature human DCs were incubated with FITC-labeled core-shell silica-NPs to determine cellular uptake. FITC labeled polystyrene cores were used as templated to generate a silica shell. Immature DCs were exposed to 200 nm silica NPs for 2 h and an image was taken in the tissue culture plate of live cells (FIG. 9 left image). All cells had taken up silica-NPs. The experiment was repeated and 6 h after exposure to the NPs, DCs were collected and spun onto glass slides using a cyto-centrifuge. In order to determine whether the NPs localize to the cell nucleus, the cells were fixed and the nuclei were stained using the nuclear dye Hoechst. The slides were analyzed by confocal microscopy (FIG. 9, right image). A few NPs were found to be localized in the nuclei (see white arrows) already at the 6 h time point. Later time points will be investigated.

Example 10

Adsorption of plasmid DNA to hollow Silica-NPs. Hollow solvent extracted Silica-NPs were resuspended in PBS and sonicated for 15 min. Different amounts of Silica-NPs were diluted in 700 mM NaCl and the dilution was mixed at 10 µl per minute with equal volume of a plasmid dilution under constant vortexing, with a total of 50 µl NP dilution and 50 µl of the DNA. After formation of the complexes, 10 µl of the mixture was resolved on a 1% agarose gel (FIG. 6). DNA adsorption to the Silica-NPs prevents the DNA from running into the gel. Instead, the DNA stays in the wells with the Silica-NPs (FIG. 6 lanes 7-14), whereas free unbound plasmid runs as two bands (FIG. 6 lanes 1 and 2). A dose response of DNA adsorption to increased amounts of NPs was observed. 2 µg plasmid DNA were completely adsorbed by 50 µl of a 0.95 mg/ml Silica-NP solution. Some free plasmid was observed when 50 µl of a 0.48 mg/ml NP solution were used. 6 mg of plasmid were completely adsorbed by 50 µl of a 3.8 mg/ml NP solution. NPs were analyzed to determine if they could be functionalized for enhanced DNA adsorption.

Figure 10:
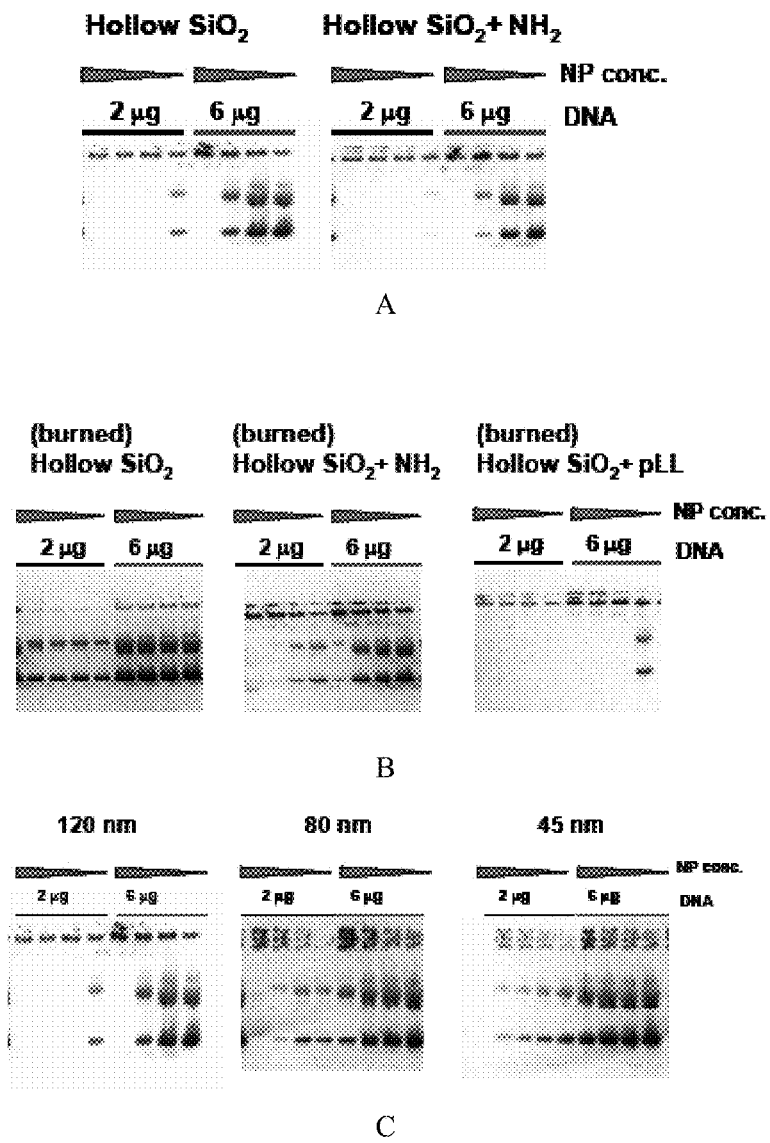
FIG. 10A-C shows adsorption of DNA to hollow silica-NPs. 2 μg or 6 μg plasmid DNA were complexed with different amounts (0.48-3.8 mg/ml) of hollow silica-NPs. The same NP concentrations are used in all of the gels. Plasmid only, nanoparticles only, as well as the complexes were resolved on a 1% agarose gel at 100V for 1 h. A) Comparison of hollow solvent extracted unmodified and NH2-modified silica NPs. B) Comparison of burned hollow silica NPs with different surface modifications: unmodified, aminemodified, and poly-L-Lysine (pLL) modified. C) Comparison of DNA adsorption to different size (120, 80, and 45 nm) unmodified solvent extracted silica-NPs.

A comparison of unmodified hollow silica-NPs and modified hollow silica-NPs with additional surface amine groups (+NH2) (FIG. 10A). These hollow Silica-NPs were functionalized with 3-aminopropyl(trimethoxy)silane as in Scheme II to add the additional amine groups. Amine-modified hollow silica NPs were able to almost completely adsorb 2 µg of plasmid DNA when using 50 µl of a 0.48 mg/ml NP solutions (FIG. 10A right gel: lane 4), whereas free plasmid DNA was detected when using the same amount of unmodified silica NPs (FIG. 10A left gel: lane 4). Thus, the addition of amine groups enhanced DNA adsorption. Although the solvent extraction procedure removes 75% of the polystyrene core, to prevent toxicity in vivo, the hollow silica NPs were burned at high heat (calcination) to completely remove any residual polystyrene. The burned hollow silica NPs with different modifications were compared for their DNA adsorption capacity (FIG. 10B). Interestingly, burned unmodified NPs bound very little, if any DNA (FIG. 10B, left gel), whereas the solvent extracted unmodified NPs effectively adsorb DNA (FIG. 10A left gel). The burning process removes the poly-Lysine chains that remained on the silica shell from the templating technique and thus removes the positive charges that allow DNA adsorption. Modified silica-NPs with additional poly-L lysine (pLL) on the surface of burned NPs was the most potent for DNA adsorption, even 6 µg plasmid DNA was completely adsorbed by 50 al of 0.95 mg/ml NPs (FIG. 10B, right gel). The amine modified silica-NPs only contain short positively charged chains (see Scheme II), whereas poly-L lysine are long chains with many amine groups. Therefore poly-L lysine coating allows for more charge-charge interactions between the NP and the DNA and therefore stronger binding capacity. The ability of different size solvent extracted unmodified hollow silica-NPs to adsorb DNA (FIG. 10C) were compared. Although all sized were able to adsorb DNA, larger 120 nm NPs showed increased DNA adsorption.

Example 11

Hollow silica-NP-DNA complexes are stable. Since the complexes were generated in the presence of 700 mM NaCl and the physiological salt concentration is 150 mM, the salt was exchanged with media prior to exposure of DCs to reduce toxicity. The Silica-NP-DNA complexes were sonicated for 15 min, spun down at 6000 rpm for 10 minutes, and resuspended in culture media. To test whether the plasmid would be released from the Silica-NPs during these steps, aliquots were taken before sonication, post sonication, from the supernatant after the spin, and from the resuspended pellet (FIG. 7). At all stages of the process the plasmid DNA remained adsorbed to the Silica-NPs and thus in the wells of the gel, indicating that neither sonication nor spinning caused a release of the plasmid DNA from the Silica-NPs. Both unmodified (U) and amine-modified (C) NPs showed the same result.

Example 12

Preparation of Silica-Iron Ethoxide Precursor 25 mg of iron (III) ethoxide is dissolved in 1 mL of absolute ethanol. The solution is then filtered using a 0.22 µm syringe microfilter to remove any solids. 10 µL of the iron (III) ethoxide solution is then added to 25 µL of hydrolyzed tetramethoxysilane and vortexed for 30 seconds to give a homogenous, translucent orange solution.

Synthesis of Iron Doped Hollow Silica Spheres with 200 nm Amine Polystyrene Beads.

To 50 µL of 2.5% w/v 200 nm amine polystyrene beads was added to 1 mL of an alcohol, either methanol or ethanol, in a 2 mL eppendorf tube. The beads were suspended and 200 µL of 0.1% poly-L-lysine solution was added and the solution was mixed for 1 minute. 35 µL of the silica-iron ethoxide precursor was then added and the solution stirred at 3000 rpm on a vortex agitator for 60 minutes at room temperature. The yellow-orange colloid is then collected via centrifugation. The supernatant is removed and 1 mL of deionized water is added. The precipitate is resuspended in the water using a vortex and collected again using centrifugation. The washing step is repeated two more times and then the precipitate is dried in a vacuum oven at 50° C. for 24 hours. The dried precipitate is then calcined at 500° C. for 48 hours to remove the polystyrene core. Up to 10% iron incorporation is observed by EDAX in the SEM photomicrographs, which may impart biodegradability over the long term.

Synthesis of Hollow Silica Spheres with Encapsulated Magnetic Iron Oxide Nanoparticles Using 200 nm Amine Polystyrene Beads.

To 50 µL of 2.5% w/v 200 nm amine polystyrene beads was added to 500 µL of a 5% dichloromethane ethanol solution (v/v) in a 2 mL eppendorf tube and suspended using a vortex agitator. 10 µL of 1.4% (w/v) magnetic iron oxide nanoparticles (5 nm) were then added to the solution and mixed for 30 seconds. The beads were allowed to swell in the solvent for 2 hours, with 10 second agitation occurring every 20 minutes. 750 µL of methanol was then added and the solution mixed and allowed to sit at room temperature for 12 hours. The solvent was reduced to a volume of 250 µL and 750 µL of 0.1M phosphate buffer solution was added and the solution mixed. 200 µL of 0.1% poly-L-lysine solution was added and the solution was mixed for 1 minute. 25 µL of 1M hydrolyzed tetramethoxysilane was then added and stirred at 3000 rpm on a vortex agitator for 10 minutes. The orange-brown precipitate is then collected in the tube using a magnet. The supernatant along with any non-magnetic particles are removed and 1 mL of deionized water is added. The precipitate is resuspended using a vortex agitator and then recollected using centrifugation. This process is repeated two more times and the precipitate is dried in a vacuum oven at 50° C. for 24 hours. The dried precipitate is then calcined at 500° C. for 48 hours to remove the polystyrene core. This permits magnetic manipulation of the silica nanospheres.

The following references are incorporated herein in their entirety. 1. a) Pablo M. Arnal, Massimiliano Comotti, Ferdi Schuth, Angew, Chem. Int. Ed. 2006, 45, 8224-8227. b) Yufang Zhu, Jianlin Shi, Weihua Shen, Xiaoping Dong, Jingwei Feng, Meilin Ruan, Yongsheng Li, Angew, Chem. Int. Ed. 2006, 44, 5083. c) H. Wang, Z. Y. Yang, Y. F. Lu. J. Appl. Phys. 2007, 101, 033129. d) Xiangling Xu, Stanford A. Asher. J. Am. Chem. Soc. 2004, 126, 7940. e) Pu Jin, Qianwang Chen, Liqing Hao, Ruifen Tian, Lixin Zhang, and Lin Wang. J. Phys. Chem. B 2004, 108, 6311. f) Igor I. Slowing, Brian G. Trewyn, Supratim Giri, Victor S.-Y. Lin. Adv. Funct. Mater. 2007, 17, 1225. 2. a) S. Y. Chang, L. Liu, S. A. Asher. J. Am. Chem. Soc. 1994, 116, 6739. B) H. Yao, Y. Takada, N. Kitamura. Langmuir 1998, 14, 595. c) D. Wu, X. Ge, Z. Zhang, M. Wang, S. Zhang. Langmuir 2004, 20, 5192. d) I. Tissot, C. Novat, F. Lefebvre, E. Bourgeat-Lami. Macromolecules 2001, 34, 5737. e) K. P. Velikov, A. van Blaaderen. Langmuir 2001, 17, 4779. 3. a) Xuefeng Ding, Kaifeng Yu, Yanqiu Jiang, Hari-Bala, Hengbin Zhang, Zichen Wang. Materials Letters 2004, 58, 3618. b) W. Wu, D. Caruntu, A. Martin, M. H. Yu, C. J. O'Connor, W. L. Zhou, J-F. Chen. Journal of Magnetism and Magnetic Materials 2007, 311, 578. 4. Jeroen Cornelissen, Eric Connor, Ho-Cheol Kim, Victor Lee, Teddie Magibitang, Philip Rice, Willi Volksen, Linda Sundberg, Robert Miller. Chem. Comm. 2003, 24, 1010. 5. Ziyi Zhong, Yadong Yin, Byron Gates, Younan Xia. Adv. Mater. 2000, 12, 206. 6. a) Frank Caruso, Heinz Lichtenfeld, Michael Giersig, Helmuth Mohward. J. Am. Chem. Soc. 1998, 120, 8623. b) Frank Caruso, Rachel A. Caruso, Helmuth Mohward. Science 1998, 282, 1111. 7. Jennifer N. Cha, Galen D. Stucky, Daniel E. Morse, Timothy J. Deming. Nature 2000, 403, 289. 8. Kjeld J. C. van Bommel, Jong Hwa Jung, Seiji Shinkai. Adv. Mater. 13, 1472. 9. Bros M, et a. J Immunolo. 2003; 171(4): 1825-34. 10. Mordmueller B, et al. EMBO rep. 2003; 4(1): 82-7. 11. Cornelissen et al. Chem Commun. pp. 1010-1011, 2003.

Although a number of embodiments and features have been described above, it will be understood by those skilled in the art that modifications and variations of the described embodiments and features may be made without departing from the teachings of the disclosure or the scope of the invention as defined by the appended claims.

What is claimed is:

1. A method for preparing a colloidal dispersion of nanospheres comprising:
    (a) depositing a silica-shell precursor on a polyamino acid or carboxylate functionalized template particle at a pH range from 5.5 to 9.5 to afford core-shell nanospheres;
    (b) subjecting said core-shell nanospheres to calcination or washing with an organic solvent to remove the template particle and to form hollow silica nanospheres; and
    (c) sonicating a solution comprising said hollow silica nanospheres to prepare a colloidal dispersion, wherein the colloidal dispersion of nanospheres is suitable for in vivo administration by injection.

2. The method of claim 1, further comprising hydrolyzing a silicon-containing compound to synthesize the silica shell precursor.

3. The method of claim 1, wherein the template particle is a polymer particle.

4. The method of claim 1, wherein the silica-shell precursor comprises a mixture of silicon and iron ethoxide.

5. The method of claim 3, wherein the template particle comprises polystyrene.

6. The method of claim 1, wherein the size of the template particle is from about 10 nm to 1 µm.

7. The method of claim 2, wherein the silicon-containing compound is selected from the group consisting of tetraalkoxysilanes, trialkoxysilanes, dialkoxysilanes, tetrapropoxysilane, tetraethoxysilane, tetramethoxysilane and any combination thereof.

8. The method of claim 2, wherein the silicon-containing compound is hydrolyzed in an acidic solution.

9. The method of claim 1, wherein the polyamino acids comprise homo- or co-polymers of amino acids with primary amine groups on the polymer backbone.

10. The method of claim 1, wherein the polyamino acid is selected from the group consisting of poly-L-lysine, poly-L-arginine and polyornithine.

11. The method of claim 1, wherein the calcination comprises heating to about 450° C.

12. The method of claim 11, wherein heating is achieved by employing a temperature ramp rate of from about 0.1° C./min to about 10° C./min.

13. The method of claim 8, wherein the acidic solution comprises hydrochloric acid, sulfuric acid, nitric acid or any combination thereof.

14. The method of claim 8, wherein the silicon-containing compound is hydrolyzed in an aqueous solution comprising about 0.01 M hydrochloric acid.

15. The method of claim 8, wherein the concentration of the silicon-containing compound in the acidic solution is about 0.1-10 M.

16. The method of claim 8, wherein the concentration of the silicon-containing compound in the acidic solution is about 1 M.

17. The method of claim 5, wherein the depositing the silica shell precursor on the polystyrene template particle is conducted at room temperature.

18. The method of claim 17, wherein the depositing the silica-shell precursor on the polystyrene template particle occurs at about pH 7.4.

19. The method of claim 17, wherein the depositing the silica-shell precursor on the polystyrene template particle occurs in a phosphate buffer.

20. The method of claim 17, wherein the polystyrene core is removed by heating in air at about 400-900° C. for 3-6 hours.

21. The method of claim 5, wherein the washing with the organic solvents to remove the template particle core utilizes an organic solvent selected from the group consisting of toluene, dichloromethane, chloroform, tetrahydrofuran, dimethylformamide, and any combination thereof.

22. The method of claim 21, wherein the polystyrene core is removed by washing the core-shell nanospheres in toluene.

23. The method of claim 1, wherein the template particle comprises latex.

* * * * *